(12) United States Patent
Yuan et al.

(10) Patent No.: US 8,476,034 B2
(45) Date of Patent: Jul. 2, 2013

(54) METHODS AND COMPOSITIONS FOR ASSAYING HOMOCYSTEINE

(75) Inventors: Chong-Sheng Yuan, San Diego, CA (US); Abhijit Datta, San Marcos, CA (US); Chao Dou, San Diego, CA (US)

(73) Assignee: General Atomics, San Diego, CA (US)

( * ) Notice: Subject to any disclaimer, the term of this patent is extended or adjusted under 35 U.S.C. 154(b) by 748 days.

(21) Appl. No.: 11/969,803

(22) Filed: Jan. 4, 2008

(65) Prior Publication Data

US 2008/0305507 A1 Dec. 11, 2008

Related U.S. Application Data

(63) Continuation-in-part of application No. 11/394,457, filed on Mar. 31, 2006, now abandoned, which is a continuation of application No. 10/801,623, filed on Mar. 15, 2004, now Pat. No. 7,097,968.

(60) Provisional application No. 60/486,865, filed on Jul. 10, 2003.

(51) Int. Cl.
*C12Q 1/48* (2006.01)

(52) U.S. Cl.
USPC .................. 435/15; 435/18; 435/25; 435/26

(58) Field of Classification Search
USPC ................................................. 435/15, 18
See application file for complete search history.

(56) References Cited

U.S. PATENT DOCUMENTS

| | | | |
|---|---|---|---|
| 4,281,061 A | 7/1981 | Zuk et al. | |
| 4,478,934 A | 10/1984 | Sato et al. | |
| 4,609,626 A | 9/1986 | Yamada et al. | |
| 4,940,658 A | 7/1990 | Allen et al. | |
| 4,981,801 A | 1/1991 | Suzuki et al. | |
| 5,631,127 A | 5/1997 | Sundrehagen | |
| 5,780,256 A | 7/1998 | Ueda et al. | |
| 5,827,645 A | 10/1998 | Sundrehagen | |
| 5,854,023 A | 12/1998 | Hillman et al. | |
| 5,861,294 A | 1/1999 | Cowart et al. | |
| 5,885,767 A | 3/1999 | Rozzell, Jr. | |
| 5,958,717 A | 9/1999 | Sundrehagen | |
| 5,985,540 A | 11/1999 | Tan et al. | |
| 6,063,581 A | 5/2000 | Sundrehagen | |
| 6,376,210 B1 | 4/2002 | Yuan | |
| 6,436,658 B1 | 8/2002 | Seman | |
| 6,610,504 B1 | 8/2003 | Yuan | |
| 6,664,073 B1 | 12/2003 | Kawasaki et al. | |
| 6,686,172 B2 | 2/2004 | Matsuyama et al. | |
| 2002/0119507 A1 | 8/2002 | Kishimoto et al. | |
| 2002/0123088 A1 | 9/2002 | Matsuyama et al. | |
| 2003/0138872 A1 | 7/2003 | Kawasaki et al. | |
| 2005/0009128 A1* | 1/2005 | Yuan et al. ....................... | 435/15 |

FOREIGN PATENT DOCUMENTS

| | | |
|---|---|---|
| CN | 1560610 | 1/2005 |
| EP | 1 295 947 | 3/2003 |
| EP | 0 726 322 | 7/2003 |
| JP | 60-172292 | 9/1985 |
| JP | 61-047195 | 3/1986 |
| JP | 4-278099 | 10/1992 |
| JP | 4686454 | 5/2011 |
| WO | WO-93/15220 | 8/1993 |
| WO | WO-00/40973 | 7/2000 |
| WO | WO-00/77244 | 12/2000 |
| WO | WO-01/02600 | 1/2001 |
| WO | WO-02/02802 | 1/2002 |
| WO | WO-03/040694 | 5/2003 |
| WO | WO-03/060478 | 7/2003 |
| WO | WO-2005/008252 | 1/2005 |
| WO | WO-2007/087541 | 8/2007 |

OTHER PUBLICATIONS

Dorgan, KM et al. An enzyme-coupled continuous spectrophotometric assay for S-adenosylmethionine-dependent methyltransferases. Analytical Biochemistry. 2006. 350: 249-255.*
Hendricks, CL et al. An enzyme-coupled colorimetric assay for S-adenosylmethione-dependent methyltransferases. Analytical Biochemistry. 2004. 326: 100-105.*
Guanhua Xue, Foreign Country Medical Surgery Fascicule (2002) 29:16-18 (with English Translation).
Office Action from Chinese Patent Application No. 200480026009.4, dated Dec. 4, 2009 (with English Translation).
Judgment, Issued as a Mandate, from *General Atomics v. Axis-Shield ASA*, US Court of Appeals for the Federal Circuit, Case No. 2007-1349, filed Jun. 5, 2008.
Office Action from EP Application No. 04 777 969.9-2404, dated Jun. 27, 2008.
Withdrawal Letter to the German Court in Dusseldorf, filed by Axis-Shield, from *Axis-Shield ASA v. DiaSys GmbH*, dated Jul. 31, 2008.
Withdrawal Letter to the German Court in Dusseldorf, filed by DiaSys, from *Axis-Shield ASA v. DiaSys GmbH*, dated Aug. 6, 2008.
Withdrawal Letter to the German Patent Court, from Nullity Action against DE 693 04 511, dated Aug. 7, 2008.
Withdrawal Letter to the EPO, from Opposition against EP 0 726 322, dated Aug. 7, 2008.
Office Action from Chinese Patent Application No. 200480026009.4, dated Mar. 6, 2009.
Judgment and Opinion, entered May 12, 2008, filed May 19, 2008.
Court Docket from PACER, *General Atomics v. Axis-Shield ASA*, US Court of Appeals for the Federal Circuit, Case No. 2007-1349, docket accessed May 29, 2008.

(Continued)

*Primary Examiner* — Allison Ford
*Assistant Examiner* — Susan E Fernandez
(74) *Attorney, Agent, or Firm* — Morrison & Foerster LLP (57) ABSTRACT

This invention relates generally to the field of homocysteine detection. In particular, the invention provides a method for determining homocysteine presence or concentration in samples, which method comprises: contacting a sample containing or suspected of containing Hcy with a Hcy co-substrate and a Hcy converting enzyme in a Hcy conversion reaction to form a Hcy conversion product and a Hcy co-substrate conversion product; and assessing the Hcy co-substrate conversion product to determine the presence, absence and/or amount of the Hcy in the sample. The Hcy co-substrate conversion product may be assessed directly, or it may be assessed by further conversion of the Hcy co-substrate conversion product into another material by the action of one or more additional enzymes. A kit for assaying homocysteine based on the same principle is also provided.

20 Claims, 2 Drawing Sheets

OTHER PUBLICATIONS

Notice of Reasons for Rejection (with English translation) for JP 2006-518957, mailed Apr. 20, 2010, 13 pages.
English Translation of CN 1560610, Jan. 2005.
Araki et al., J. Chromatog. (1987) 422:43-52.
Ballal et al., Cleveland Clinic Journal of Medicine (1997) 64:543-549.
Boers et al., J. Inher. Metab. Dis. (1997) 20:301-306.
Boushey et al., JAMA (1995) 274:1049-1057.
Cornell and Riscoe, Biochim. Biophys. Acta (1998) 1396(1):8-14.
Coulter-Karis and Hershfield, Ann. Hum. Genet. (1989) 53(2):169-175.
Diaz-Arrastia et al., Arch. Neurol. (1998) 55:1407-1408.
Donnelly et al., Ann. Clin. Biochem. (2000) 37:194-198.
Ducloux et al., Nephrol. Dial. Transplantl. (1998) 13:2890-2893.
Foody et al., Clinician Reviews (1998) 8:203-210.
Frantzen et al., Clinical Chemistry 44:2, 311-316 (1998).
Gore, Int. J. Biochem., 13(8):879-86 (1981).
Hornberger et al., American J. of Public Health, 88:61-67 (1998).
Jacobsen et al., Clin. Chem., 44:2238-2239 (1998).
Lai et al.,.Mol. Cell. Biol., 17(5):2413-24 (1997).
Mansoor et al., Anal. BioChem., 200:218-229 (1992).
Matsuyama et al., Clinical Chemistry, 47:2155-2156 (2001).
McNally et al., Biochem. Biophys. Res. Commun. 231:645-650 (1997).
Moghadasian et al., Arch. Intern. Med., 157:2299-2307 (1997).
Perez-De La Mora et al., Anal. Biochem., 180(2):248-52 (1989).
Perry, "Homocystinuria" in Nyhan W.L. ed., Heritable disorders of amino acid metabolism. New York, John Wiley & Sons, pp. 395-428 (1974).
Refsum et al., Annu. Rev. Medicine, 49:31-62 (1998).
Saksela and Raivio, Biochem. J., 315(1):235-9 (1996).
Scott et al., "The etiology of neural tube defects" in Graham, I., Refsum, H., Rosenberg, I.H., and Ureland P.M. ed. "Homocysteine metabolism: from basic science to clinical medicine" Kluwer Academic Publishers, Boston, pp. 133-136 (1995).
Shapiro, Biochim. Biophys. Acta. 29:405-9 (1958).
Shapiro et al., J. Biol. Chem., 239(5):1551-6 (1964).
Sigma-Aldrich catalog No. A5168.
Sigma-Aldrich catalog No. 01898.
Sigma-Aldrich catalog No. A9876.
Sigma-Aldrich catalog No. A1030.
Sigma-Aldrich catalog No. BCR647.
Sigma-Aldrich catalog No. 59023.
Sigma-Aldrich catalog No. 61311.
Sigma-Aldrich catalog No. 61306.
Sigma-Aldrich catalog No. K4388.
Sigma-Aldrich catalog No. P1903.
Sigma-Aldrich catalog No. P5788.
Sigma-Aldrich catalog No. 83330.
Singh et al., Eur. J. Biochem. 241:564-571 (1996).
Stabler et al., J. Clin. Invest., 81:466-474 (1988).
Stehouwer et al., Kidney International, 55:308-314 (1999).
Stein et al., Arch. Intern. Med., 158:1301-1306 (1998).
Tan et al., Clinical Chemistry, 49:1029-1030 (2003).
Thanbichler et al., J. Bacteriol., 181(2):662-5 (1999).
Thomas et al., J. Biol. Chem., 275(52):40718-24 (2000).
Ueland et al., J. Lab. Clin. Med., 114:473-501 (1989).
Ueland et al., Clin. Chem., 39:1764-1779 (1993).
International Search Report for PCT/US2004/022218, mailed on Jan. 7, 2005, 4 pages.
Nelson et al., Lehninger Principles of Biochemistry, $3^{rd}$ ed., Worth Publishers (2000) pp. 640-642.
Shapiro, Methods Enzymol. (1971) 17(Pt. B):400-405.
Chagoya De Sanchez et al., Int. J. Biochem. (1991) 23(12):1439-1443.
Kuchino et al., Cancer Research (1977) 37:206-208.
Aitken et al., Biochemistry (2003) 42(2):571-578.
Amara et al., Neurosci. Lett. (1995) 185(3):147-150.
Bergmeyer, (ed.) Methods of Enzymatic Analysis, VCH Verlagsgesellschaft MBH., Weinheim, DE, 7:110-117 ($3^{rd}$ ed. 1985).
Bergmeyer, (ed.) Methods of Enzymatic Analysis, VCH Verlagsgesellschaft MBH., Weinheim, DE, 7:357-364 ($3^{rd}$ ed. 1985).
Bergmeyer, (ed.) Methods of Enzymatic Analysis, VCH Verlagsgesellschaft MBH., Weinheim, DE, 7:403-409 ($3^{rd}$ ed. 1985).
Bobbitt et al., Introduction to Chromatography, Reinold Book Corporation, p. 2.
Cantoni, Annu. Rev. Biochem. (1975) 44:435-451.
Cantoni, J. Biol. Chem. (1953) 204:403-416.
Chu and Hall, Am. J. Clin. Path. (1988) 90(4):446-449.
Clarke et al., New England Journal of Medicine (1991) 324(17):1149-1155.
Clarke et al., New England Journal of Medicine (1991) 325(13):966-967.
Esaki and Soda, Methods in Enzymology (1987) 143:459-465.
Fung et al., Analytical Chemistry (1979) 51(14):2319-2324.
Hammerl et al., J. Immunol. Methods (1993) 165:59-66.
Khuntirat and Lucher, J. Virol. Methods (1990) 29:97-103.
Kolhouse et al., Archives of Biochemistry and Biophysics (1993) 303:355-360.
Kredich et al., Anal. Biochem. (1981) 116(2):503-510.
Kumar et al., Biochemistry (1983) 22(4):762-768.
Lackie and Dow, The Dictionary of Cell and Molecular Biology ($3^{rd}$ ed.), Academic Press, 1999 at p. 101.
Lavine et al., Biochim. Biophys. Acta. (1982) 717(1):76-85.
Markham et al., J. Biol. Chem. (1980) 255(19):9082-9092.
McGraw-Hill Dictionary of Scientific and Technical Terms ($5^{th}$ ed.), Parker (ed.), McGraw-Hill Inc, p. 686.
Ohshima et al., J. Biol. Chem. (1978) 253:5719-5725.
Ohshima and Soda, Eur. J. Biochem. (1979) 100:29-39.
Osifo, Enzyme (1978) 23:116-120.
Ravindranath, Principles and Practice of Chromatography, Chapter 1, Vistas of Chromatography, pp. 24-52.
Refsum et al., Clin. Chem. (1985) 31(4):624-628.
Refsum et al., Clin. Chem. (1989) 35:1921-1927.
Russell, J. Biol. Chem. (1944) 156:457.
Shapiro et al., Journal of Biol. Chem. (1965) 240(6):2512-2518.
Sicard et al., Prep. Biochem. (1978) 8(1):19-36.
Sliwinski and Doty, Agric. Food Chem. (1958) 6(1):41.
Soda, Anal. Biochem. (1968) 25:228-235.
Soda et al., Multifunctional biocatalysis: methionine $\gamma$-lyase (Elsevier Science Publishers B.V., Amsterdam 1983).
Soda et al., $4^{th}$ European Congress on Biotechnology (1987) 4:713-717.
Stabler et al., Analytical Biochemistry (1987) 162:185-196.
Stryer, (ed.) Biochemistry ($3^{rd}$ ed.), W.H. Freeman and Company, pp. 177-178.
Tanaka et al., Enzyme Micro. Technol. (1985) 7:530-537.
Tanaka et al., Sulfur-containing Amino Acids (1979) 2:313-322 (and English Translation).
Tanaka et al., Annual Meetings of the Agricultural Chemical Society of Japan, Nagoya, p. 106 (1978) (and English Translation).
Tanaka et al., Agric. Biol. Chem. (1981) 45(4):1021-1022.
Tanaka et al., Biochem. (1977) 16(1):100-106.
Totani et al., Biochem. Soc. Trans. (1986) 14(6):1172-1173.
Trewyn and Kerr, Federation Proceedings (1977) 36(3):718.
Walker and Barrett, Int. J. Parasitol. (1997) 27(8):883-897.
Yasukochi and Masters, J. Biol. Chem. (1976) 251(17):5337-5344.
Diazyme Homocysteine Assay Kit (Enzymatic Cycling) product insert.
Package Insert of Diazyme's Microplate STE-Based Assay of Homocysteine.
Notice of Opposition to EP Patent 0 726 322, filed Jan. 16, 2004.
Patentee's Response to the Notices of Opposition, filed Oct. 1, 2004.
Response to Patentee's letter dated Oct. 1, 2004, filed Jul. 11, 2005.
Tanaka et al., Analytical Letters (1981) 14:111-118.
Selim and Greenberg, JBC (1958) 234:1474-1480.
Kashiwamata et al., Biochim. Biophys. Acta (1970) 212:488-500.
Binkley, JBC (1951) 101:531-534.
Shimizu et al., Biotechnol. Appl. Biochem. (1986) 8:153-159.
Porter et al., JBC (1991) 32:21616-21625.
Trewyn and Kerr, Journal of Biochemical and Biophysical Methods (1981) 4:299-307.
Loughlin et al., JBC (1964) 239:2888-2895.
Graham, Trends Cardiovasc. Med. (1991) 1:244-249.
Garras et al., Analytical Biochem. (1991) 199:112-118.

Frisell et al., JBC (1953) 207:709-716.
Sullivan and Hess, JBC (1936) 116:221-233.
EC4.2.1.22, www.chem.qmul.ac.uk/iubmb/enzyme/EC4/2/1/22.html.
Yamaguchi and Hosokawa, Methods in Enzymology (1987) 143:395-403.
Kotb and Kredich, J. Biol. Chem. (1985) 260(7):3923-30.
Tanaka et al., J. Applied Biochem. (1980) 2:439-444.
Bruton and Cox, Eur. J. Biochem. (1979) 100:301-308.
Homogeneous Enzymic Homocysteine Reagent package insert from Carolina Liquid Chemistries.
Complaint for Patent Infringement and Unfair Competition and Demand for Jury Trial, filed Oct. 9, 2001.
First Amended Complaint for Patent Infringement and Demand for Jury Trial, filed Dec. 19, 2001.
Answer to Amended Complaint and Counterclaim; Jury Demand, filed Jan. 8, 2002.
Plaintiff Axis-Shield ASA's Early Neutral Evaluation Conference Settlement Brief, filed Mar. 11, 2002.
Stipulation for Joint Dismissal Without Prejudice of Complaint and Counter-Claim; [Proposed] Order, filed Mar. 22, 2002.
Complaint for Declaratory Relief, filed Oct. 11, 2005.
Answer and Counterclaim of Axis-Shield ASA, filed Oct. 27, 2005.
General Atomics' Reply to Counterclaim, filed Nov. 16, 2005.
Reply and Counterclaim of Carolina Liquid Chemistries Corporation, filed Nov. 16, 2005.
Answer to Counterclaim of Carolina Liquid Chemistries Corporation, filed Nov. 17, 2005.
Joint Case Management Conference Statement, filed Feb. 10, 2006.
General Atomics' Amended Complaint for Declaratory Relief, filed Mar. 1, 2006.
General Atomics' Amended Reply to Counterclaim, filed Mar. 1, 2006.
Carolina Liquid Chemistries Corporation's Amended Reply and Counterclaim, filed Mar. 1, 2006.
Axis-Shield's Disclosure of Asserted Claims and Preliminary Infringement Contentions (Patent L.R. 3-1), filed Mar. 3, 2006.
Initial Disclosures Pursuant to FRCP Rule 26 for Defendant and Counterclaimant Axis-Shield, filed Mar. 3, 2006.
General Atomics and Carolina Liquid Chemistries' Initial Disclosure Statement, filed Mar. 3, 2006.
General Atomics and Carolina Liquid Chemistries' Notice of Motion, Motion, and Memorandum of Points and Authorities for Summary Adjudication of Noninfringement, filed Apr. 14, 2006.
Declaration of Anders T. Aannestad in Support of General Atomics and Carolina Liquid Chemistries' Motion for Summary Adjudication of Noninfringement, filed Apr. 14, 2006.
Declaration of Ronald T. Borchardt in Support of General Atomics and Carolina Liquid Chemistries' Motion for Summary Adjudication of Noninfringement, filed Apr. 14, 2006.
Declaration of Chong Yuan, Ph.D. in Support of General Atomics and Carolina Liquid Chemistries' Motion for Summary Adjudication of Noninfringement, filed Apr. 14, 2006.
Declaration of Dr. Dongyuan Xia in Support of General Atomics and Carolina Liquid Chemistries' Motion for Summary Adjudication of Noninfringement, filed Apr. 14, 2006.
Declaration of Dr. Chao in Support of General Atomics and Carolina Liquid Chemistries' Motion for Summary Adjudication of Noninfringement, filed Apr. 14, 2006.
[Proposed] Order on General Atomics and Carolina Liquid Chemistries' Motion for Summary Adjudication of Noninfringement, filed Apr. 14, 2006.
General Atomics and Carolina Liquid Chemistries' Corrected Preliminary Invalidity Contentions, filed Apr. 17, 2006.
General Atomics and Carolina Liquid Chemistries' Exchange of Proposed Terms and Claim Elements for Construction, filed May 1, 2006.
Axis-Shield's Proposed Terms and Claim Elements for Construction (Patent L.R. 4-1), filed May 1, 2006.
Axis-Shield's Memorandum of Points and Authorities in Opposition to General Atomics' and Carolina Liquid Chemistries' Motion for Summary Adjudication of Noninfringement, filed May 12, 2006.
Declaration of Timothy P. Walker in Support of Axis-Shield's Opposition to General Atomics' and Carolina Liquid Chemistries' Motion for Summary Adjudication of Noninfringement, filed May 12, 2006.
Declaration of Ralph Green in Support of Axis-Shield's Opposition to General Atomics' and Carolina Liquid Chemistries' Motion for Summary Adjudication of Noninfringement, filed May 12, 2006.
General Atomics and Carolina Liquid Chemistries' Reply In Support of Motion for Summary Adjudication of Noninfringement, filed May 19, 2006.
Declaration of Ronald T. Borchardt in Support of General Atomics and Carolina Liquid Chemistries' Reply In Support of Motion for Summary Adjudication of Noninfringement, filed May 19, 2006.
Declaration of Anders T. Aannestad in Support of General Atomics and Carolina Liquid Chemistries' Reply in Support of Motion for Summary Adjudication of Noninfringement, filed May 19, 2006.
General Atomics and Carolina Liquid Chemistries' Preliminary Claim Construction and Extrinsic Evidence, filed May 26, 2006.
Axis-Shield's Preliminary Constructions of Terms and Claim Elements for Construction (Patent L.R. 4-2), filed May 26, 2006.
Court Hearing—MSJ on Noninfringement, Jun. 2, 2006.
Letter from Axis-Shield to the European Patent Office for EP 0 726 322, dated Jun. 13, 2001.
Letter and attached description on a homocysteine assay using homocysteinase, from Axis-Shield to the European Patent Office for EP 0 726 322, dated Nov. 3, 1999.
Letter from Axis-Shield to the European Patent Office for EP 0 726 322, dated Jan. 4, 1999.
Summons to Attend Oral Proceedings for EP 0 726 322, dated May 24, 2006.
Joint Further Case Management Conference Statement, filed Jun. 16, 2006.
Joint Claim Construction and Prehearing Statement, filed Jun. 17, 2006.
Axis-Shield's Notice of Motion and Motion to Amend Preliminary Infringement Contentions; Memorandum of Points and Authorities in Support, filed Jun. 30, 2006.
Declaration of Timothy P. Walker In Support of Axis-Shield's Motion to Amend Preliminary Infringement Contentions, filed Jun. 30, 2006.
Axis-Shield's Motion to Shorten Time to Hear Motion to Amend Preliminary Infringement Contentions; Memorandum of Points and Authorities in Support, filed Jun. 30, 2006.
Declaration of Timothy P. Walker In Support of Axis-Shield's Motion to Shorten Time to Hear Motion to Amend Preliminary Infringement Contentions, filed Jun. 30, 2006.
General Atomics and Carolina Liquid Chemistries' Opposition to Axis-Shield's Motion to Shorten Time to Hear Motion to Amend Preliminary Infringement Contentions, filed Jul. 6, 2006.
Declaration of Anders T. Aannestad in Support of General Atomics and Carolina Liquid Chemistries' Opposition to Axis-Shield's Motion to Shorten Time to Hear Motion to Amend Preliminary Infringement Contentions, filed Jul. 6, 2006.
Order Granting Plaintiff's Motion for Summary Judgment, filed Jul. 19, 2006.
General Atomics and Carolina Liquid Chemistries' Opposition to Axis-Shield's Motion to Amend Preliminary Infringement Contentions, filed Jul. 21, 2006.
Declaration of Anders T. Aannestad in Support of General Atomics and Carolina Liquid Chemistries' Opposition to Axis-Shield's Motion to Amend Preliminary Infringement Contentions, filed Jul. 21, 2006.
Deposition of Ronald Borchardt, Ph.D., taken Jul. 25, 2006.
Axis-Shield's Reply Memorandum in Support of its Motion to Amend Preliminary Infringement Contentions, filed Jul. 26, 2006.
Supplemental Declaration of Timothy P. Walker in Support of Axis-Shield's Motion to Amend Preliminary Infringement Contentions, filed Jul. 26, 2006.
Deposition of Ralph Green, M.D., Ph.D., taken Aug. 1, 2006.
General Atomics and Carolina Liquid Chemistries' Request for Leave to File Surreply in Opposition to Axis-Shield's Motion to Amend Preliminary Infringement Contentions, filed Aug. 1, 2006.
Declaration of Anders T. Aannestad in Support of General Atomics and Carolina Liquid Chemistries' Request for Leave to File Surreply in Opposition to Axis-Shield's Motion to Amend Preliminary Infringement Contentions, filed Aug. 1, 2006.
Axis-Shield's Memorandum in Opposition to General Atomics' Request for Leave to File Surreply, filed Aug. 2, 2006.
Order Granting Request for Leave to File Surreply in Opposition to Axis-Shield's Motion to Amend Preliminary Infringement Contentions, filed Aug. 4, 2006.
Axis-Shield's Opening Claim Construction Brief, filed Aug. 7, 2006.
[Proposed] Order Construing Claims, filed Aug. 7, 2006.
Declaration of Ralph Green in Support of Axis-Shield's Proposed Claim Constructions, filed Aug. 7, 2006.
Declaration of Timothy P. Walker in Support of Axis-Shield's Proposed Claim Constructions, filed Aug. 7, 2006.
General Atomics and Carolina Liquid Chemistries' Surreply to Axis-Shield's Motion to Amend Preliminary Infringement Contentions, filed Aug. 8, 2006.
Order Granting Defendant's Motion to Amend Preliminary Infringement Contentions, filed Aug. 9, 2006.
General Atomics and Carolina Liquid Chemistries' Responsive Claim Construction Brief, filed Aug. 21, 2006.
Declaration of Ronald T. Borchardt in Support of General Atomics and Carolina Liquid Chemistries' Responsive Claim Construction Brief, filed Aug. 21, 2006.
Declaration of Anders T. Aannestad in Support of General Atomics and Carolina Liquid Chemistries' Responsive Claim Construction Brief, filed Aug. 21, 2006.
[Proposed] Order Construing Claims, filed Aug. 21, 2006.
De La Haba and Cantoni, The Journal of Biological Chemistry (1959) 234(3):603-608.
Finkelstein and Martin, The Journal of Biological Chemistry (1984) 259(15):9508-9513.
Fux et al., Am. J. Physiol. Renal Physiol. (2005) 289:F786-F792.
German et al., The Journal of Biological Chemistry (1983) 258(18):10997-11003.
Kredich et al., Analytical Biochemistry (1981) 116:503-510.
Molloy et al., Biomedical Chromatography (1990) 4(6):257-260.
Shapiro and Yphantis, Biochimica et Biophysica Acta (1959) 36:241-244.
Shimizu et al., Biotechnology and Applied Biochemistry (1986) 8:153-159.
Ueland et al., The Journal of Biological Chemistry (1984) 259(4):2360-2364.
Ueland and Refsum, Nord. Med. (1989) 104:293-298.
Axis-Shield's First Amended Disclosure of Asserted Claims and Preliminary Infringement Contentions (Patent L.R. 3-1), filed Aug. 11, 2006.
[Corrected Proposed] Order Construing Claims, filed Aug. 28, 2006.
Axis-Shield's Reply Claim Construction Brief, filed Aug. 28, 2006.
Declaration of Elaine Y. Chow in Support of Axis-Shield's Reply Claim Construction Brief, filed Aug. 28, 2006.
Amended [Proposed] Order Construing Claims, filed Aug. 28, 2006.
Supplemental Joint Claim Construction Statement, filed Sep. 15, 2006.
Amended Errata Sheet for the Deposition of Ronald Borchardt, Ph.D., dated Aug. 23, 2006.
Claim Construction Order, filed Sep. 27, 2006.
General Atomics and Carolina Liquid Chemistries' Second Notice of Motion, Motion, and Memorandum of Points and Authorities for Summary Judgment of Noninfringement, filed Oct. 26, 2006.
Declaration of Ronald T. Borchardt in Support of General Atomics and Carolina Liquid Chemistries' Second Motion for Summary Judgment of Noninfringement, filed Oct. 26, 2006.
Declaration of Chong Yuan, Ph.D. in Support of General Atomics and Carolina Liquid Chemistries' Second Motion for Summary Judgment of Noninfringement, filed Oct. 26, 2006.
Declaration of Dongyuan Xia, Ph.D. in Support of General Atomics and Carolina Liquid Chemistries' Second Motion for Summary Judgment of Noninfringement, filed Oct. 26, 2006.
Declaration of Anders T. Aannestad in Support of General Atomics and Carolina Liquid Chemistries' Second Motion for Summary Judgment of Noninfringement, filed Oct. 26, 2006.
Axis-Shield's Disclosure of Asserted Claims and Final Infringement Contentions, filed Oct. 30, 2006.
Application as filed on Mar. 15, 2004, U.S. Appl. No. 10/801,623.
Non-Final Office Action from U.S. Appl. No. 10/801,623, mailed on Jun. 3, 2005.
Amendment in Response to Non-Final Office Action, from U.S. Appl. No. 10/801,623, filed Nov. 3, 2005.
Notice of Allowance from U.S. Appl. No. 10/801,623, mailed on Feb. 8, 2006.
Axis-Shield's Memorandum of Points and Authorities in Opposition to Second Motion for Summary Judgment of Noninfringement by General Atomics and Carolina Liquid Chemistries, filed Dec. 22, 2006.
Declaration of Elisabeth Try Valoe in Opposition to General Atomics and Carolina Liquid Chemistries Second Motion of Summary Judgment of Noninfringement, filed Dec. 22, 2006.
Declaration of Frank Frantzen in Opposition to General Atomics and Carolina Liquid Chemistries Second Motion of Summary Judgment of Noninfringement, filed Dec. 22, 2006.
Declaration of Arne Kristian Nordhei in Opposition to General Atomics and Carolina Liquid Chemistries Second Motion of Summary Judgment of Noninfringement, filed Dec. 22, 2006.
Declaration of Arne Ludvig Faaren in Opposition to General Atomics and Carolina Liquid Chemistries Second Motion of Summary Judgment of Noninfringement, filed Dec. 22, 2006.
Transcript of Claim Construction Hearing on Sep. 13, 2006.
Defendant Axis-Shield ASA's Response to General Atomics' Second Set of Requests for Admissions, filed Jan. 12, 2007.
General Atomics and Carolina Liquid Chemistries' Reply in Support of Second Motion for Summary Judgment of Non-Infringement, filed Feb. 9, 2007.
Declaration of Chong Yuan in Support of General Atomics and Carolina Liquid Chemistries' Reply in Support of Second Motion for Summary Judgment of Non-Infringement, filed Feb. 9, 2007.
Declaration of Dr. Xihua Cao in Support of General Atomics and Carolina Liquid Chemistries' Reply in Support of Second Motion for Summary Judgment of Non-Infringement, filed Feb. 9, 2007.
Declaration of Ronald T. Borchardt in Support of General Atomics and Carolina Liquid Chemistries' Reply in Support of Second Motion for Summary Judgment of Non-Infringement, filed Feb. 9, 2007.
Declaration of Dr. Xiao-Kun Zhang in Support of General Atomics and Carolina Liquid Chemistries' Reply in Support of Second Motion for Summary Judgment of Non-Infringement, filed Feb. 9, 2007.
Declaration of Anders T. Aannestad in Support of General Atomics and Carolina Liquid Chemistries' Reply in Support of Second Motion for Summary Judgment of Non-Infringement, filed Feb. 9, 2007.
Surreply Declaration of Frank Frantzen in Opposition to General Atomics and Carolina Liquid Chemistries Second Motion of Summary Judgment of Non-Infringement, filed Feb. 20, 2007.
Axis-Shield's Surreply Memorandum of Points and Authorities in Opposition to General Atomics and Carolina Liquid Chemistries Second Motion for Summary Judgment of Non-Infrengement, filed Feb. 20, 2007.
Surreply Declaration of Timothy P. Walker in Opposition to General Atomics and Carolina Liquid Chemistries Second Motion of Summary Judgment of Non-Infringement, filed Feb. 21, 2007.
Transcript of Summary Judgment Hearing on Feb. 23, 2007.
Order Granting Plaintiff's Motion for Summary Judgment in Part and Denying it in Part, filed Apr. 11, 2007.
Stipulation of Dismissal Without Prejudice of General Atomics', Carolina Chemistries', and Axis-Shield's Remaining Claims and Counterclaims Regarding the '127 and '717 Patents and [Proposed] Order, filed Apr. 30, 2007.
Final Judgment, filed May 2, 2007.
Axis Shield ASA's Notice of Appeal, filed May 3, 2007.
Brief of Defendant/Counterclaimant-Appellant Axis-Shield ASA, filed Jul. 30, 2007, Case No. 2007-1349 at the US Court of Appeals for the Federal Circuit.
Hamann, (ed.), Introductory Chemistry, $2^{nd}$ ed., Pearson Prentice Hall (2006) pp. 54-55.
Letter Regarding the Opposition Procedure, dated Aug. 4, 2006.
Letter Regarding the Opposition Procedure, dated Sep. 4, 2006.

Patentee's Final Written Submissions in Opposition for EP 0 726 322, dated Sep. 5, 2006.
Minutes of the Oral Proceedings Before the Opposition Division for EP 0 726 322, dated Nov. 16, 2006.
Interlocutory Decision in Opposition Proceedings for EP 0 726 322, dated Feb. 21, 2007.
Notice of Appeal for EP 0 726 322, dated May 2, 2007.
Patentee's Notice of Appeal for EP 0 726 322, dated May 3, 2007.
Statement of Grounds of Appeal for Opposition to EP 0 726 322, dated Jul. 2, 2007.
Patentee's Statement of Grounds of Appeal to EP 0 726 322, dated Jul. 3, 2007.
Stipulation and [Proposed] Order Dismissing '645 and '581 Patents with Prejudice, filed Feb. 15, 2006.
Stipulation and [Proposed] Order Re: Axis-Shield's Answer and Counterclaim to the Amended Complaint, filed Mar. 23, 2006.
Transcript of Claim Construction Tutorial Hearing on Sep. 13, 2006.
General Atomics' Claim Construction Tutorial Presentation, Sep. 13, 2006.
Axis-Shield's Claim Construction Tutorial Presentation, Sep. 13, 2006.
General Atomics' Claim Construction Presentation, Sep. 13, 2006.
Axis-Shield's Claim Construction Presentation, Sep. 13, 2006.
General Atomics and Carolina Liquid Chemistries' Objections to Evidence, Notice of Motion, Motion and Memorandum of Points and Authorities in Support of Motion to Strike, filed Feb. 9, 2007.
Declaration of Anders T. Aannestad in Support of General Atomics and Carolina Liquid Chemistries' Objections to Evidence, Notice of Motion, Motion and Memorandum of Points and Authorities in Support of Motion to Strike, filed Feb. 9, 2007.
General Atomics' Second Motion for Summary Judgment of Noninfringement Presentation, Feb. 23, 2007.
Axis-Shield's Opposition to Second Motion for Summary Judgment of Noninfringement Presentation, Feb. 23, 2007.
Notice of Correction of Appeal Brief of Defendant/Counterclaimant-Appellant Axis-Shield ASA, filed Oct. 5, 2007, Case No. 2007-1349 at the US Court of Appeals for the Federal Circuit.
Brief of Plaintiff-Appellee General Atomics, Diazyme Laboratories Division and Counterclaim Defendant-Appellee Carolina Liquid Chemistries Corporation, filed Nov. 13, 2007, Case No. 2007-1349 at the US Court of Appeals for the Federal Circuit.
Reply Brief of Defendant/Counterclaimant-Appellant Axis-Shield ASA, filed Nov. 30, 2007.
Joint Appendix, filed Dec. 7, 2007.
Court Docket from PACER for *General Atomics* v. *Axis-Shield*, United States District Court for the Northern District of California, docket accessed Apr. 25, 2008.
Court Docket from PACER, *General Atomics* v. *Axis-Shield ASA*, US Court of Appeals for the Federal Circuit, Case No. 2007-1349, docket accessed Apr. 25, 2008.
Reply to the Patentee's Statement of Grounds of Appeal, dated Nov. 27, 2007.
Axis Shield's Administrative Motion to File Documents Under Seal Pursuant to Local Rule 79-5, filed Dec. 22, 2006.
Order Granting Defendants' Administrative Motion to File Document Under Seal Pursuant to Local Rule 79-5, filed Jan. 8, 2007.
Declaration of Michael D. Toney in Opposition to General Atomics and Carolina Liquid Chemistries Second Motion of Summary Judgment of Noninfringement, filed Dec. 22, 2006.
Declaration of Elaine Y. Chow in Support of Axis-Shield's Opposition to General Atomics and Carolina Liquid Chemistries' Second Motion of Summary Judgment of Noninfringement, filed Dec. 22, 2006.
Amended Stipulated Protective Order, filed Mar. 2, 2006.
Confidential Deposition of Ronald T. Borchardt, Ph.D., taken Nov. 28, 2006.
Confidential Deposition of Dong Yuan Xia, Ph.D., taken Nov. 29, 2006.
Confidential Deposition of Chong Yuan, taken Nov. 30, 2006.
General Atomics, Diazyme Laboratories Division's Response to Axis-Shield ASA's Interrogatories, Set One, filed Jan. 18, 2007.
Carolina Liquid Chemistries' Response to Axis-Shield ASA's Interrogatories, Set One, filed Jan. 19, 2007.
Confidential Declaration of Anders T. Aannestad in Support of General Atomics and Carolina Liquid Chemistries' Reply in Support of Second Motion for Summary Judgment of Noninfringement, filed Feb. 9, 2007.
Declaration of Elaine Y. Chow in Support of Axis-Shield's Sur-Reply in Opposition to General Atomics and Carolina Liquid Chemistries' Second Motion for Summary Judgment of Noninfringement, filed Feb. 21, 2007.
Confidential Deposition of Michael D. Toney, taken Jan. 22, 2007.
Confidential Deposition of Arne Nordhei, taken Jan. 23, 2007.
Confidential Deposition of Arne Ludwig Faaren, taken Jan. 24, 2007.
Confidential Deposition of Elisabeth Valoe, taken Jan. 25, 2007.
Confidential Deposition of Frank Frantzen, taken Jan. 26, 2007.
Nullity Action against German Patent DE 693 04 511 T2, filed Nov. 13, 2007.
Complaint, filed Oct. 1, 2007, from *Axis-Shield ASA* v. *DiaSys GmbH*, Dusseldorf, Germany (in German).
Statement of Defence, filed May 2, 2008, from *Axis-Shield ASA* v. *DiaSys GmbH*, Dusseldorf, Germany (in German and with English translation).
Axis-Shield Reply from Nullity Action against German Patent DE 693 04 511 T2, filed Apr. 29, 2008.
Decision to grant a European patent from EP 04777969.9, dated Aug. 4, 2011, 1 page.
Office Action (translation) from CN 201010134298.7, dated Aug. 31, 2011, 4 pages.
Office Action from EP 09700710.8, dated Sep. 16, 2011, 4 pages.
Notice of Allowance for CN 200480026009.4, dated Jul. 27, 2011, 4 pages.
Notice of Allowance for JP 2006-518957, dated Feb. 2, 2011, 3 pages.
Response to Office Action from EP 09700710.8, Aug. 12, 2011, 5 pages.
Office Action from EP Application No. 04 777 969.9-2404, dated Oct. 1, 2009, 5 pages.
Supplementary European Search Report for EP 09 70 0710, mailed on Feb. 3, 2011, 5 pages.
European Search Report for EP 10 18 1606, mailed on Jan. 26, 2011, 6 pages.
Office Action from Chinese Patent Application No. 200480026009.4, dated Jun. 28, 2010.
Amendment to Japanese Patent Application No. 2006-518957, filed Sep. 21, 2010.
Response to Office Action from Chinese Patent Application No. 200480026009.4, filed Sep. 2, 2010.
Response submitted for European Patent Application No. EP10181606.4 on Dec. 17, 2012, 17 pages.
Communication Pursuant to Article 94(3) EPC for EP 10 181 606.4, mailed Aug. 8, 2012, 5 pages.

* cited by examiner

Figure 1. Co-Substrate Conversion Product Based Enzyme Cycling Assay of Homocysteine

Figure 2

METHODS AND COMPOSITIONS FOR ASSAYING HOMOCYSTEINE

CROSS-REFERENCE TO RELATED APPLICATIONS

This application is a continuation in part of U.S. patent application Ser. No. 11/394,457, filed Mar. 31, 2006, which is a continuation of U.S. patent application Ser. No. 10/801,623, now U.S. Pat. No. 7,097,968, which claims the priority benefit of provisional application U.S. Ser. No. 60/486,865, filed Jul. 10, 2003; the contents of each of these applications are incorporated by reference in their entirety.

TECHNICAL FIELD

This invention relates generally to the field of homocysteine detection. In particular, the invention provides a method for determining homocysteine (Hcy) presence or concentration in samples in which homocysteine reacts with a Hcy co-substrate in a Hcy conversion reaction catalyzed by a Hcy converting enzyme to form a Hcy conversion product and a Hcy co-substrate conversion product, and the Hcy co-substrate conversion product is assessed to determine the presence and/or concentration of the Hcy in the sample. The Hcy co-substrate can be assessed directly, or it can be further converted into one or more other materials before assessment is done. A kit for assaying homocysteine based on the same principle is also provided.

BACKGROUND OF THE INVENTION

Total concentration of homocysteine in body fluids, such as plasma or serum, is an important marker for disease. For example, homocysteine quantification can be an important risk indicator for cardiovascular disease, can be a sensitive marker of cobalamin and folate deficiencies, and can be used to diagnose in-born errors in metabolism known as homocystinuria. Homocysteine quantification has also been reported as useful in assessing birth defects in pregnant women and cognitive impairment in the elderly. See Frantzen, et al., Enzyme Conversion Immunoassay for Determining Total Homocysteine in Plasma or Serum, Clinical Chemistry 44:2, 311-316 (1998).

Homocysteine (Hcy) is a thiol-containing amino acid formed from methionine during S-adenosylmethionine-dependent transmethylation reactions. Intracellular Hcy is remethylated to methionine, or is irreversibly catabolized in a series of reactions to form cysteine. Intracellular Hcy is exported into extracellular fluids such as blood and urine, and circulates mostly in oxidized form, and mainly bound to plasma protein (Refsum, et al., *Annu. Rev. Medicine,* 49:31-62 (1998)). The amount of Hcy in plasma and urine reflects the balance between Hcy production and utilization. This balance may be perturbed by clinical states characterized by genetic disorders of enzymes involved in Hcy transsulfuration and remethylation (e.g., cystathionine β-synthase and $N^{5,10}$-methylenetetrahydrofolate reductase or dietary deficiency of vitamins (e.g., vitamin $B_6$, $B_{12}$ and folate) involved in Hcy metabolism (Baual, et al., *Cleveland Clinic Journal of Medicine,* 64:543-549 (1997)). In addition, plasma Hcy levels may also be perturbed by some medications such as antifolate drugs (e.g., methotrexate) used for treatments of cancer or arthritis (Foody, et al., *Clinician Reviews,* 8:203-210 (1998))

Severe cases of homocysteinemia are caused by homozygous defects in genes encoding for enzymes involved in Hcy metabolisms. In such cases, a defect in an enzyme involved in either Hcy remethylation or transsulfuration leads to as much as 50-fold elevations of Hcy in the blood and urine. The classic form of such a disorder, congenital homocysteinemia (Hcyemia), is caused by homozygous defects in the gene encoding cystathionine β-synthase (CBS). These individuals suffer from thromboembolic complications at an early age, which result in stroke, myocardial infarction, renovascular hypertension, intermittent claudication, mesenteric ischemic, and pulmonary embolism. Such patients may also exhibit mental retardation and other abnormalities resembling ectopia lentis and skeletal deformities (Perry T., *Homocysteine*: Selected aspects in Nyham W. L. ed. *Heritable disorders of amino acid metabolism.* New York, John Wiley & Sons, pp. 419-451 (1974)). It is also known that elevated Hcy levels in pregnant women is related to birth defects of children with neurotube closures (Scott, et al., "*The etiology of neural tube defects*" in Graham, L, Refsum, H., Rosenberg, I. H., and Ureland P. M. ed. "*Homocysteine metabolism: from basic science to clinical medicine*" Kluwer Academic Publishers, Boston, pp. 133-136 (1995)). Thus, the diagnostic utility of Hcy determinations has been well documented in these clinical conditions.

It has been demonstrated that even mild or moderately elevated levels of Hcy also increase the risk of atherosclerosis of the coronary, cerebral and peripheral arteries and cardiovascular disease (Boushey, et al., *JAMA,* 274:1049-1057 (1995)). The prevalence of Hcyemia was shown to be 42%, 28%, and 30% among patients with cerebral vascular disease, peripheral vascular disease and cardiovascular disease, respectively (Moghadasian, et al., *Arch. Intern. Med.,* 157: 2299-2307 (1997)). A meta-analysis of 27 clinical studies calculated that each increase of 5 μM in Hcy level increases the risk for coronary artery disease by 60% in men and by 80% in women, which is equivalent to an increase of 20 $mg/dl^{-1}$ (0.5 $mmol/dl^{-1}$) in plasma cholesterol, suggesting that Hcy, as a risk factor, is as strong as cholesterol in the general population. Results from these clinical studies concluded that hyperhomocysteinemia is an emerging new independent risk factor for cardiovascular disease, and may be accountable for half of all cardiovascular patients who do not have any of the established cardiovascular risk factors (e.g., hypertension, hypercholesterolemia, cigarette smoking, diabetes mellitus, marked obesity and physical inactivity).

Mild homocysteinemia is mainly caused by heterozygosity of enzyme defects. A common polymorphism in the gene for methylenetetrahydrofolate reductase appears to influence the sensitivity of homocysteine levels to folic acid deficiency (Boers, et al., *J. Inher. Metab. Dis.,* 20:301-306 (1997)). Moreover, plasma homocysteine levels are also significantly increased in heart and renal transplant patients (Ueland, et al., *J. Lab. Clin. Med.,* 114:473-501 (1989)), Alzheimer patients (Jacobsen, et al., *Clin. Chem.,* 44:2238-2239 (1998)), as well as in patients of non-insulin-dependent diabetes mellitus (Ducloux, et al., *Nephrol. Dial. Transplantl,* 13:2890-2893 (1998)). The accumulating evidence linking elevated homocysteine with cardiovascular disease has prompted the initiation of double-blind, randomized and placebo controlled multicenter clinical trials to demonstrate the efficacy of lowering plasma Hcy in preventing or halting the progress of vascular disease (Diaz-Arrastia, et al., *Arch. Neurol.,* 55:1407-1408 (1998)). Determination of plasma homocysteine levels should be a common clinical practice.

As a risk factor for cardiovascular disease, the determination of total plasma Hcy levels (reduced, oxidized and protein-bound) has been recommended in clinical setting (Hornberger, et al., *American J. of Public Health,* 88:61-67 (1998)).

Since 1982, several methods for determining total plasma Hcy have been described (Mansoor, et al., *Anal. BioChem.*, 200:218-229 (1992); Steir, et al., *Arch. Intern. Med.*, 158: 1301-1306 (1998); Ueland, et al., *Clin. Chem.*, 39:1764-1779 ( ) 1993); and Ueland, et al., "*Plasma homocysteine and cardiovascular disease*" in Francis, R. B. Jr. eds. *Atherosclerotic Cardiovascular Disease, Hemostasis, and Endothelial Function.* New York, Marcel Dokker, pp. 183-236 (1992); see, also, Ueland, et al., "*Plasma homocysteine and cardiovascular disease*" in Francis, R. B. Jr. eds. *Atherosclerotic Cardiovascular Disease, Hemostasis, and Endothelial Function.* New York, Marcel Dokker, pp. 183-236 (1992)). The assay of total Hcy in plasma or serum is complicated by the fact that 70% of plasma Hcy is protein-bound and 20-30% exists as free symmetric or mostly asymmetric mixed disulfides. Free reduced Hcy exists in only trace amounts (Stehouwer, et al., *Kidney International*, 55:308-314 (1999)). Most of the methods require sophisticated chromatographic techniques such as HPLC, capillary gas chromatography, or mass spectrometry (GC/MS) to directly or indirectly (e.g., enzymatic conversion of Hcy to SAH (S-adenosylhomocysteine) by SAH hydrolase followed by HPLC or TLC separation) measure Hcy. Radioenzymatic conversion of Hcy to radiolabeled SAH by SAH hydrolase prior to TLC separation has also been used. In these assays, chromatographic separation, which is often time-consuming and cumbersome to perform, is a common key step of these methods. More particularly, these methods require highly specialized and sophisticated equipment and well-trained analytic specialists. The use of such equipment is generally not well-accepted in routine clinical laboratory practice. Immunoassays for Hcy that use a monoclonal antibody against SAH (Araki, et al., *J. Chromatog.*, 422:43-52 (1987)) are also known. These assays are based upon conversion of Hcy to SAH, which is then detected by a monoclonal antibody. Monoclonal antibody against albumin-bound Hcy has been developed for determination of albumin-bound Hcy (Stabler, et al., *J. Clin. Invest.*, 81:466-474 (1988)), which is the major fraction of total plasma Hcy. Other immunological protocols are also available (see, e.g., U.S. Pat. Nos. 5,631,127, 5,827,645, 5,958,717, 6,063,581 and 5,885,767). Though immunoassays avoid a time-consuming chromatographic separation step and are amenable to automation, production of monoclonal antibody is expensive, somewhat unpredictable, and often requires secondary or even tertiary antibodies for detection. Recently, enzymatic methods for homocysteine assay have been reported (Matsuyama, et al., *Clinical Chemistry*, 47:2155-2156 (2001); Tan et al., *Clinical Chemistry*, 49:1029-1030 (2003); U.S. Pat. Nos. 5,885,767; 5,998,191; 6,046,017; 6,174,696; 6,664,073; and 6,436,658), all of these describe homocysteine assays based on the assessment of homocysteine conversion products generated by homocysteine converting enzymes.

Other methods for determining homocyteine in a sample are described in U.S. Pat. No. 6,686,172 and U.S. Pat. App. Pub. No. 2002/0119507.

An efficient and accurate assay, that can be carried out without necessity for highly skilled personnel or complex analytical chemistry equipment, has been needed. The present invention addresses the above and other related concerns in the art.

BRIEF SUMMARY OF THE INVENTION

In one aspect, the present invention is directed to an assay for homocysteine in a sample. According to this assay, a sample containing or suspected of containing homocysteine (Hcy) is contacted with a Hcy co-substrate and a Hcy converting enzyme in a Hcy conversion reaction to form a Hcy conversion product and a Hcy co-substrate conversion product; and the Hcy co-substrate conversion product is assessed to determine the presence, absence and/or amount of the Hcy in said sample.

In some embodiments of the invention, the Hcy co-substrate conversion product is assessed without chromatographic separation.

In some embodiments, the Hcy co-substrate is S-adenosylmethionine (SAM), the Hcy converting enzyme is S-adenosylmethionine (SAM)-dependent homocysteine S-methyltransferase, the Hcy conversion product is methionine (Met) and the Hcy co-substrate conversion product is S-adenosyl-L-homocysteine (SAH), and the SAH is assessed to determine the presence, absence and/or amount of the Hcy in the sample.

SAM for these assays can be used in any suitable form. It may be added to the sample directly. In some embodiments, SAM is produced in an assay mixture in situ, by an additional reaction between ATP and methionine, catalyzed by SAM synthase. In these embodiments, ATP and methionine and SAM synthase are included in the assay mixture; they may be added either before or during the assay. Accordingly, where SAM is used in an assay or a kit, it can alternatively be replaced by ATP, methionine and SAM synthase.

The SAH may be converted to Hcy and adenosine (Ado), and Ado is assessed to determine the presence, absence and/or amount of the Hcy in the sample. In some embodiments, the SAH is contacted with a SAH hydrolase to generate Hcy from SAM, which is cycled into the Hcy conversion reaction by the SAM-dependent homocysteine S-methyltransferase to form a Hcy co-substrate based enzyme cycling reaction system, and adenosine (Ado), which is assessed to determine the presence, absence and/or amount of the Hcy in the sample.

The Ado may be assessed by any suitable methods known in the art such as immunological or enzymatic methods. The Ado may be assessed directly or indirectly. For example, the Ado may be assessed indirectly by assessing a co-substrate or a reaction product of adenosine conversion by an adenosine converting enzyme. In some embodiments, the adenosine converting enzyme is an adenosine kinase and the reaction product is Adenosine 5'-monophosphate. In other embodiments, the adenosine converting enzyme is an adenosine deaminase and the reaction products are ammonium and inosine.

In other embodiments, SAH can be converted into Adenine and S-ribosyl homocysteine by an adenosylhomocysteine nucleosidase (E.C. 3.2.2.9). The S-ribosyl homocysteine can be converted into Hcy and ribose by an S-ribosyl homocysteinase (E.C. 3.2.1.148), which permits the Hcy to re-enter the initial reaction with SAM and homocysteine methyltransferase (HMTase), forming a cyclic reaction process. The adenine formed in this cyclic reaction process can be detected to measure the extent of the reaction, which correlates with the concentration of Hcy present in the sample. Alternatively, the ribose formed by this step can be detected.

Adenine can be detected directly, such as by an adenine-specific antibody, using methods such as those discussed above. Alternatively, adenine can be detected by conversion to other materials that are readily detected spectrophotometrically. In some embodiments, adenine is converted by an adenine deaminase enzyme (E.C. 3.5.4.2) into $NH_3$ (ammonia) and hypoxanthine. Either ammonia or hypoxanthine can then be detected using methods such as an antibody specific for hypoxanthine, or by monitoring an enzymatic reaction known to efficiently consume free ammonia. Hypoxanthine can also be measured by using a Trinder reaction, to detect hydrogen peroxide formed from hypoxanthine in the presence of xanthine oxidase.

One embodiment of this method uses glutamate dehydrogenase (GLDH) to convert the ammonia formed by the action of adenine deaminase, along with added α-ketoglutarate, into glutamate. This reaction concurrently oxidizes NADH into $NAD^+$, and can be readily monitored spectrophotemetrically by observing the disappearance of NADH or the appearance of $NAD^+$ by known methods.

Another embodiment of this method uses an adenine phosphoribosyltransferase (EC 2.4.2.7) and 5-phospho-α-D-ribose 1-diphosphate (PRPP) into AMP and diphosphate; formation of either AMP or diphosphate can then be monitored by known methods. Methods for specific detection of AMP, such as by selective antibody binding, are known in the art. In one aspect, the present invention is directed to a method for assaying homocysteine (Hcy) in a sample, which method comprises: a) contacting a sample containing or suspected of containing Hcy with a Hcy co-substrate and a Hcy converting enzyme in a Hcy conversion reaction to form a Hcy conversion product and a Hcy co-substrate conversion product, wherein the Hcy co-substrate is S-adenosylmethionine (SAM), the Hcy converting enzyme is S-adenosylmethionine (SAM)-dependent homocysteine S-methyltransferase, the Hcy conversion product is methionine (Met) and the Hcy co-substrate conversion product is S-adenosyl-L-homocysteine (SAH), and b) assessing the SAH to determine the presence, absence and/or amount of the Hcy in the sample, wherein the SAH is assessed without chromatographic separation.

The SAH may be assessed by any suitable methods known in the art such as immunological or enzymatic methods. For example, SAH may be assessed by assessing binding between SAH and mutant SAH binding enzyme, e.g., a mutant SAH hydrolase that has binding affinity for Hcy, SAH or adenosine but has attenuated catalytic activity. Preferably, the assessment of SAH does not involve an enzymatic reaction generating $H_2O_2$ and detection of $H_2O_2$.

In another example, the SAH may be assessed by using an antibody which specifically binds to the SAH. The antibody may be monoclonal or polyclonal. The antibody may also be bound to a carrier matrix. Any suitable immunoassay formats, e.g., sandwich and competition assay formats, can be used.

In some embodiments, SAH is converted by an adenosyl-homocysteine nucleosidase into adenine and S-ribosyl homocysteine. In these examples, adenine or S-ribosyl homocysteine can be detected. It is sometimes convenient to detect adenine directly, or to detect adenine by converting it into ammonia and hypoxanthine by the activity of an adenine deaminase. Ammonia is then detected by a conventional method, such as by monitoring the formation of NAD+ or the disappearance of NADH as ammonia and a-ketoglutarate react to form glutamate, in the presence of glutamate dehydrogenase. In other examples, hypoxanthine is detected either directly or by its conversion into another conversion product such as xanthine, which may be catalyzed by a hypoxanthine-consuming enzyme such as xanthine oxidase. In other examples, adenine is detected by its conversion into AMP and disphophate, catalyzed by adenine phosphoribosyltransferase in the presence of added 5-phospho-α-D-ribose 1-diphosphate (PRPP).

The methods of the invention may be used for assaying homocysteine in any sample, including, but not limited to, a body fluid or a biological tissue. The body fluid may be selected from the group consisting of urine, blood, plasma, serum, saliva, semen, stool, sputum, cerebral spinal fluid, tears, mucus and amniotic fluid. In some embodiments, the body fluid is blood. In some embodiments, the blood sample is further separated into a plasma or serum fraction.

In some embodiments, prior to or concurrently with the contact between the sample and the Hcy co-substrate and the Hcy converting enzyme, oxidized or conjugated Hcy in the sample is converted into reduced Hcy. In some embodiments, the sample is subjected to treatment by dithiothreitol, tris(2-carboxyethyl)-phosphine hydrochloride (TCEP) or other reducing agent, in appropriate amounts to produce free homocysteine in the sample.

The method of the invention may further comprise a step of removing the reducing agent used to convert oxidized or conjugated Hcy into reduced Hcy prior to or concurrently with contacting the sample with the Hcy co-substrate and the Hcy converting enzyme. For example, the reducing agent can be removed by addition of N-ethylmaleimide or other thio-reacting compounds.

Still another aspect of the present invention is directed to a kit for determining presence or concentration of homocysteine in a sample, which kit comprises: a) a Hcy converting enzyme; b) a Hcy co-substrate; and c) a reagent for assessing Hcy co-substrate conversion product.

In some embodiments, the Hcy co-substrate is S-adenosylmethionine (SAM), the Hcy converting enzyme is a S-adenosylmethionine (SAM)-dependent homocysteine S-methyltransferase, the Hcy co-substrate conversion product is S-adenosyl-L-homocysteine (SAH), and the reagent for assessing Hcy co-substrate conversion product is a reagent for assessing SAH. In some embodiments, the kit further comprises a reagent, e.g., a SAH hydrolase, to generate Hcy from SAM, which is cycled into the Hcy conversion reaction by the SAM-dependent homocysteine S-methyltransferase to form a Hcy co-substrate based enzyme cycling reaction system, and adenosine (Ado). Optionally, ATP, methionine and SAM synthase can be included as a replacement for SAM.

The reagent for assessing SAH can comprise more than one reagent catalyzing more than one step. For example, the reagent for assessing SAH can comprise adenosylhomocysteine nucleosidase, to convert SAH into adenine and S-ribosyl homocysteine, and can further comprise additional materials for detection of adenine and/or S-ribosyl homocysteine. Examples of these materials include an antibody specific for either adenine or S-ribosyl homocysteine, or an enzyme such as adenine deaminase or adenine phosphoribosyltransferase, for further conversion of adenine into other products that are readily detected by known methods. The reagent for assessing SAH in these examples may further comprise an additional material necessary for either the conversion of SAH into other conversion products, or an additional material necessary for the detection of an SAH conversion product. Specific examples include reagents for detection of ammonia produced by the action of adenine deaminase on adenine, e.g., NADH and/or a-ketoglutarate, or PRPP and/or adenine phosphoribosyltransferase.

The invention also provides a kit for assaying Hcy in a sample, which kit comprises: a) a S-adenosylmethionine (SAM)-dependent homocysteine S-methyltransferase; b) S-adenosylmethionine (SAM), or ATP, methionine and SAM synthase; c) a SAH hydrolase; and d) a reagent for assessing adenosine (Ado). The reagent for assessing Ado may be an adenosine converting enzyme other than the SAH hydrolase, such as an adenosine kinase and an adenosine deaminase.

The invention also provides a kit for assaying Hcy in a sample, which kit comprises: a) a S-adenosylmethionine (SAM)-dependent homocysteine S-methyltransferase; b) S-adenosylmethionine (SAM), or ATP, methionine and SAM synthase; and c) a reagent for assessing SAH, wherein the kit does not comprise an enzyme or a reagent for generating $H_2O_2$ and a reagent for detecting $H_2O_2$. The reagent for assessing SAH can be, for example, SAH nucleosidase, or a reagent for the detection of adenine formed by the action of SAH nucleosidase on SAH. Alternatively, it can be a reagent for the conversion of adenine into one or more adenine conversion products, such as ammonia and hypoxanthine, or AMP and disphophate: suitable reagents for these conversions include adenine deaminase and adenine phosphoribosyltransferase.

In some embodiments, the kit of the invention further comprises a reducing agent such as dithiothreitol (DTT) or TCEP.

The kit of the invention may be in any suitable packaging and may also include instructions for practicing methods described herein. The kit may optionally include additional components such as buffers.

The assays described herein can be used for any suitable purposes, e.g., prognostic, diagnostic, drug screening or treatment monitoring purposes. The assays readily can be automated. In addition, the assays can be adapted for use in point of care systems and in home test kits. For example, blood test point of care systems can be adapted for measuring homocysteine levels using methods provided herein. Home test kits may also be adapted for use with the methods provided herein.

DETAILED DESCRIPTION OF THE INVENTION

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "homocysteine (Hcy)" refers to a compound with the following molecular formula: $HSCH_2CH_2CH(NH_2)COOH$. Biologically, Hcy is produced by demethylation of methionine and is an intermediate in the biosynthesis of cysteine from methionine. The term "Hcy" encompasses free Hcy (in the reduced form) and conjugated Hcy (in the oxidized form). Hcy can conjugate with proteins, peptides, itself or other thiols through disulfide bond.

As used herein, "homocysteine (Hcy) conversion reaction" refers to a reaction in which a compound reacts with a Hcy molecule during which a chemical group (e.g., a methyl group) is transferred from the compound to the Hcy molecule to form two reaction products. The compound that reacts with the Hcy molecule and provides the chemical group is referred to as "homocysteine (Hcy) co-substrate." The enzyme that catalyzes the reaction is referred to as "homocysteine (Hcy) converting enzyme." The reaction product that contains the whole or part of the original Hcy molecule is referred to as "homocysteine (Hcy) conversion product." The reaction product that does not contain any element from the original Hcy molecule is referred to as "Hcy co-substrate conversion product."

As used herein, "SAM-dependent homocysteine S-methyltransferase" refers to an enzyme that catalyzes formation of methionine and S-adenosyl-L-homocysteine (SAH) from homocysteine and S-adenosylmethionine (SAM). It is intended to encompass SAM-dependent homocysteine S-methyltransferase with conservative amino acid substitutions that do not substantially alter its activity.

As used herein, "SAH hydrolase" refers to an ubiquitous eukaryotic enzyme, which is also found in some prokaryotes, which catalyzes hydrolysis of SAH to adenosine (Ado) and Hcy. SAH hydrolase also catalyzes the formation of SAH from Ado and Hcy. The co-enzyme of SAH hydrolase is $NAD^+/NADH$. SAH hydrolase may have several catalytic activities. In the hydrolytic direction, the first step involves oxidation of the 3'-hydroxyl group of SAH (3'-oxidative activity) by enzyme-bound $NAD^+$ ($E-NAD^+$), followed by β-elimination of L-Hcy to give 3'-keto-4',5'-didehydro-5'-deoxy-Ado. Michael addition of water to the 5'-position to this tightly bound intermediate (5'-hydrolytic activity) affords 3'-keto-Ado, which is then reduced by enzyme-bound NADH (E-NADH) to Ado (3'-reduction activity). It is intended to encompass SAH hydrolase with conservative amino acid substitutions that do not substantially alter its activity.

As used herein the term "assessing" is intended to include quantitative and qualitative determination in the sense of obtaining an absolute value for the amount or concentration of the analyte, e.g., homocysteine or Ado, present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein, "adenosine deaminase" refers to an enzyme that catalyzes the deamination of adenosine to form inosine. It is intended to encompass adenosine deaminase with conservative amino acid substitutions that do not substantially alter its activity.

As used herein, "adenosine kinase" refers to an enzyme that catalyzes the formation of adenosine 5'-monophosphate and ADP from adenosine and ATP. It is intended to encompass adenosine kinase with conservative amino acid substitutions that do not substantially alter its activity.

As used herein, "adenine deaminase" refers to an enzyme that catalyzes the deamination of adenine to form hypoxanthine and ammonia. It is intended to encompass adenine deaminase with conservative amino acid substitutions that do not substantially alter its activity.

As used herein, "adenine phosphoribosyltransferase" refers to an enzyme that catalyzes the reaction of adenine with 5-phospho-α-D-ribose 1-diphosphate to form AMP and diphosphate. It is intended to encompass adenine phosphoribosyltransferases with conservative amino acid substitutions that do not substantially alter its activity.

As used herein, "adenosylhomocysteine nucleosidase" or "SAH nucleosidase" refers to an enzyme that catalyzes the conversion of SAH into adenine and S-ribosyl homocysteine. It is intended to encompass homocysteine nucleosedase with conservative amino acid substitutions that do not substantially alter its activity.

As used herein, "S-ribosyl homocysteinase" refers to an enzyme that catalyzes the conversion of S-ribosyl homocysteine into homocysteine and ribose. It is intended to encompass S-ribosyl homocysteinase with conservative amino acid substitutions that do not substantially alter its activity.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, "production by recombinant means" refers to production methods that use recombinant nucleic acid methods that rely on well known methods of molecular biology for expressing proteins encoded by cloned nucleic acids.

As used herein, "fluid" refers to any composition that can flow. Fluids thus encompass compositions that are in the form of semi-solids, pastes, solutions, aqueous mixtures, gels, lotions, creams and other such compositions.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "disease or disorder" refers to a pathological condition in an organism resulting from, e.g., infection or genetic defect, and characterized by identifiable symptoms.

As used herein, "antibody" includes not only intact polyclonal or monoclonal antibodies, but also fragments thereof (such as Fab, Fab', F(ab')$_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class.

B. Methods for Assaying Homocysteine

The invention provides a method for assaying homocysteine (Hcy) in a sample,
which method comprises: a) contacting a sample containing or suspected of containing Hcy with a Hcy co-substrate and a Hcy converting enzyme in a Hcy conversion reaction to form a Hcy conversion product and a Hcy co-substrate conversion product; and b) assessing said Hcy co-substrate conversion product to determine the presence, absence and/or amount of said Hcy in said sample.

In some embodiments, the Hcy co-substrate conversion product is assessed without chromatographic separation.

In some embodiments, the Hcy converting enzyme is a S-adenosylmethionine (SAM)-dependent homocysteine S-methyltransferase. When a SAM-dependent homocysteine S-methyltransferase is used as the Hcy converting enzyme, the Hcy co-substrate is S-adenosylmethionine (SAM), the Hcy conversion product is methionine (Met) and the Hcy co-substrate conversion product is S-adenosyl-L-homocysteine (SAH), and the SAH is assessed to determine the presence, absence and/or amount of the Hcy in the sample.

Any S-adenosylmethionine (SAM)-dependent homocysteine S-methyltransferase that transfers a methyl group from SAM to Hcy can be used. For example, S-adenosylmethionine:L-homocysteine S-methyltransferase described by Shapiro and Stanley K (Methods Enzymol. 17 Pt.B, Sulfur Amino acids, pp. 400-405 (1971)) and Shapiro SK (*Biochim. Biophys. Acta.* 29:405-9 (1958)) can be used. The homocysteine S-methyltransferase (EC 2.1.1.10) encoded by the nucleic acid having the following GenBank Accession No. AF297394 and the amino acid sequence having the following GenBank Accession Nos. AAG10301, CAA16035, NP_856132, NP_302039, CAD97346, T51939, T51941 and CAC30428 can also be used. Preferably, the SAM-dependent homocysteine S-methyltransferase from *Escherichia coli.* (Thanbichler et al., *J. Bacteriol.*, 181(2):662-5 (1999)) or *S. cerevisiae* (Shapiro et al., *J. Biol. Chem.*, 239(5):1551-6 (1964) and Thomas et al., *J. Biol. Chem.*, 275(52):40718-24 (2000)) can be used.

SAM for these assays can be used in any suitable form. It may be added to the sample directly. In some embodiments, SAM is produced in an assay mixture in situ, by an additional reaction between ATP and methionine, catalyzed by SAM synthase. In these embodiments, ATP and methionine and SAM synthase are included in the assay mixture; they may be added either before or during the assay. Accordingly, where SAM is used in an assay or a kit, it can alternatively be replaced by ATP, methionine and SAM synthase.

SAH may be assessed using any methods known in the art. For example, SAH may be assessed by using an antibody which specifically binds to SAH. Antibodies may be polyclonal or monoclonal. Examples of antibodies specific to SAH are described in U.S. Pat. Nos. 5,631,127 and 6,063,581. Antibodies specific for SAH can also be generated using methods known in the art, for example methods described in U.S. Pat. Nos. 5,631,127 and 6,063,581.

Any immunological assays may be used for detecting SAH with the antibody specific to SAH, for example, competition or sandwich assays in solutions or on a solid support, precipitation/aggregation assays. In some embodiments, the SAH is assessed by contacting the sample reacted with SAM-dependent homocysteine S-methyltransferase in the presence of SAM with an antibody specific to SAH and with a detectable hapten for the antibody other than the SAH, and wherein determining the presence or amount of the SAH is effected indirectly by determining the presence or amount of the detectable hapten either bound or not bound to the antibody. In some embodiments, the antibody is bound to a carrier matrix.

SAH may also be assessed using a mutant SAH hydrolase having binding affinity for SAH but has attenuated catalytic activity. These mutant SAH hydrolases and assay methods using mutant SAH hydrolases are described in U.S. Pat. No. 6,376,210 and WO 03/060478.

SAH may also be assessed by converting SAH to adenosine and Hcy by SAH hydrolase, and the adenosine generated is assessed. In some embodiments, the SAH is contacted with a SAH hydrolase to generate Hcy from SAM, which is cycled into the Hcy conversion reaction by the SAM-dependent homocysteine S-methyltransferase to form a Hcy co-substrate based enzyme cycling reaction system, and adenosine (Ado), which is assessed to determine the presence, absence and/or amount of the Hcy in the sample.

Figure 1:
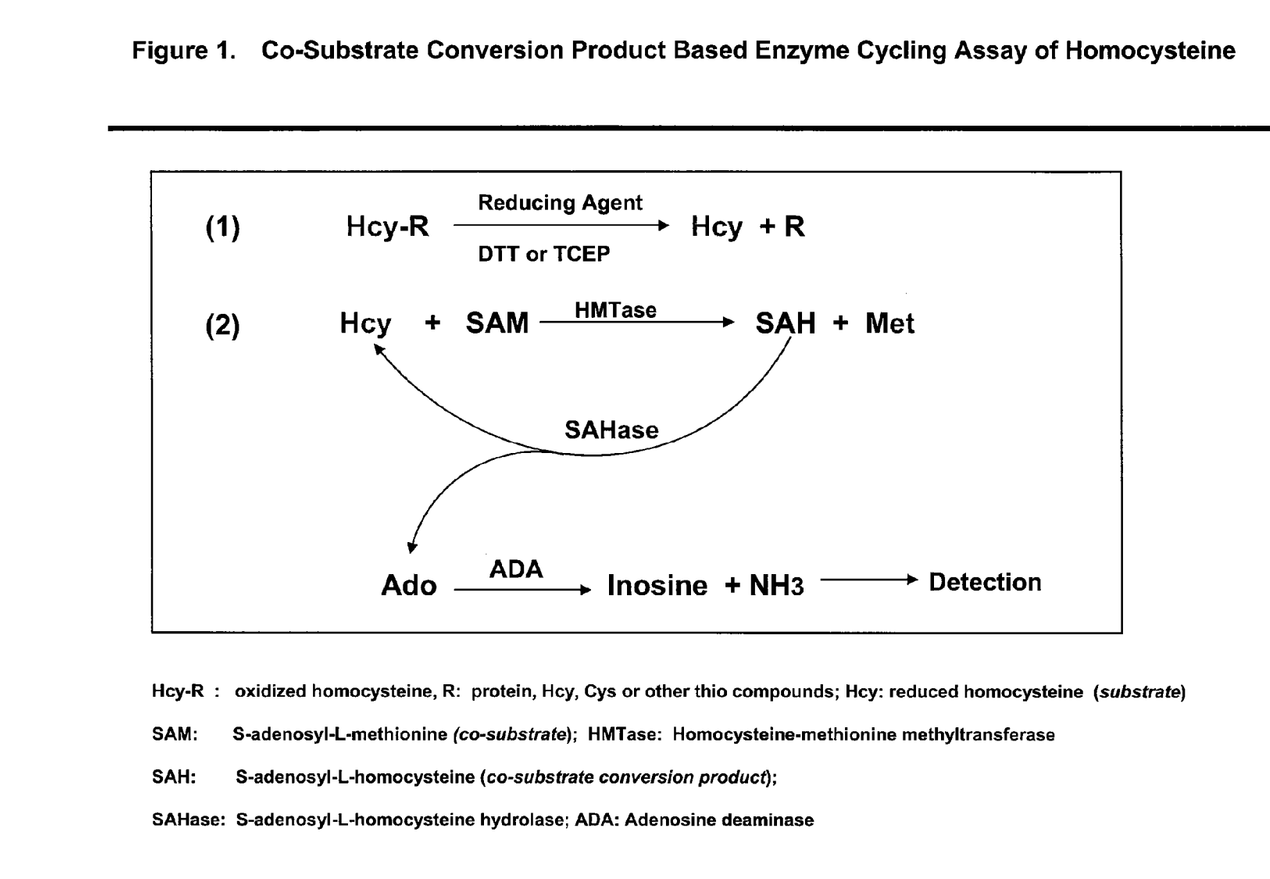
FIG. 1 illustrates an exemplary assay method for homocysteine. Hcy: L-homocysteine; SAM: S-adenosylmethionine; HMTase: SAM-dependent homocysteine S-methyltransferase; and SAHase: S-adenosyl-L-homocysteine hydrolase.

In some embodiments, the present invention provides a method for assaying homocysteine in a sample, which method comprises: a) methylating homocysteine, if present in a sample, using a methyl donor, e.g., S-adenosylmethionine (SAM) and a SAM-dependent homocysteine S-methyltransferase to form methionine and S-adenosyl-L-homocysteine (SAH); b) releasing adenosine (Ado) from said formed SAH and generating homocysteine using an enzyme S-adenosyl-L-homocysteine hydrolase; and c) assessing said released Ado to determine presence and/or amount of homocysteine in said sample. The method can further include measuring the released amounts of Ado over time. Preferably, steps a) and b) are cycled to release said Ado at rate that can be correlated to the concentration of homocysteine in the sample. Also preferably, the rate of release of the Ado is correlated with standard homocysteine values of concentration. Any suitable methyl donors and methyltransferases can be used. For example, the methyl donor can be SAM and the methylation enzyme can be a SAM-dependent homocysteine methyltransferase. Preferably, the methyl donor SAM is provided in a concentration of at least approximately 5 µM. The rate of Ado formation can be measured using any suitable methods. For example, the rate of Ado formation can be measured enzymatically. Preferably, the rate of Ado formation is measured using Ado deaminase, glutamate dehydrogenase, purine nucleoside phosphorylase, xanthine oxidase, peroxidase, adenosine kinase, or a combination of any two or more of these enzymes. These assay methods are further described herein.

Any SAH hydrolase can be used. For example, the nucleic acid molecules containing nucleotide sequences with the GenBank accession Nos. M61831-61832 can be used in obtaining nucleic acid encoding SAH hydrolase (See Coulter-Karis and Hershfield, *Ann. Hum. Genet.*, 53(2):169-175 (1989)). Also preferably, the nucleic acid molecule containing the sequence of nucleotides or encoding the amino acids described in U.S. Pat. No. 5,854,023 can be used to obtain SAH hydrolase.

Various reducing reagents can be used (for example DTT, TCEP, cysteine, mercaptoethanol, dithioerythritol, sodium borohydride, etc.), however DTT is particularly suitable, e.g., at about 5 mM concentration. DTT should itself be stored at low pH and thus the assay kit can conveniently include a solution of DTT at a low pH (e.g., about 3) but with a low buffer capacity and a separate solution of SAH-hydrolase, which may be partially or totally inactive, at substantially neutral pH and preferably buffered. When these solutions are combined, the enzyme is reactivated at neutral pH. This combination can if desired take place in the presence of the test sample, or with the test sample added shortly thereafter. The other reducing agents mentioned above may similarly be used for both SAH-hydrolase stabilization/activation. TCEP can be stored at a neutral pH, which allows the enzymes to be included in the same reagent with the reducing agent.

The Ado may be assessed by any suitable methods known in the art such as immunological or enzymatic methods. Generally methods relying upon photometric (e.g. calorimetric, spectrophotometric or fluorometric) detection and immunological methods may be used as these may particularly readily be adapted for use in clinical laboratories. Methods based on enzymatic reaction or reaction with mono- or polyclonal antibodies can also be used, as these are simple and quick and can be relatively inexpensive to perform. For example, the Ado may be assessed by monitoring the reaction with enzymes which convert it directly or indirectly to products which may be detected photometrically, e.g., spectrophotometrically. Suitable enzymes, which should of course be non-reactive with the other substrates of the homocysteine converting enzyme, particularly homocysteine, include adenosine deaminase (which converts adenosine to inosine) and adenosine kinase (which converts adenosine and ATP to ADP and phosphorylated adenosine). Such enzymes may further be combined with other enzymes which act to convert the products formed to further detectable products.

Thus exemplary Ado detection schemes useful in the assay of the invention include:

In scheme (1), an immunoassay is conducted and the fluorescein labelled adenosine can be detected.

In scheme (2), the reaction is catalyzed by an adenosine deaminase and the ammonia generated by the adenosine deaminase reaction may readily be detected using known methods, e.g., calorimetric techniques. Thus for example the ammonia generated in the sample may be reacted to form colored products, the formation of which may be detected spectraphotometrically.

In scheme (2a), the reaction is catalyzed by L-glutamate dehydrogenase and the NAD(P)$^+$ can be spectraphotometrically detected at 340 nm.

In scheme (2b1), the reaction is catalyzed by a purine nucleoside phosphorylase. In schemes (2b2) and (2b3), the reactions are catalyzed by a xanthine oxidase. In scheme (2b4), the reaction is catalyzed by a peroxidase. The inosine and uric acid have distinctive UV absorption properties and can thus be monitored spectraphotometrically, by kinetic measurements. However the use of UV detection of uric acid or inosine has certain limitations in that the sensitivity of the method is rather poor and it requires a UV-light source and a UV-transparent sample container. It may thus be more convenient to rely upon calorimetric detection of the Quinone dye at 550 nm.

Alternatively, in scheme (2b); the xanthine oxidase reaction lends itself to detection using fluorogens or chromogens, e.g., red-ox indicators, by assessing the reduction/oxidation potential, or by measuring O$_2$ consumption, or more particularly H$_2$O$_2$ formation, for example by the use of electronic sensors. Numerous red-ox indicators can be used for this purpose, and a wide range of methods are described in the literature for assaying $H_2O_2$ and $O_2$ in solution. Indeed, $H_2O_2$ is frequently detected in clinical assays. Hydrogen peroxide, for example, can also be assessed using the non enzymatic chemiluminescent reactions of peroxoxalate and the acridinium esters, the latter in aqueous solution at neutral pH.

In scheme (3), the reaction is catalyzed by an adenosine kinase. In scheme (3a), the reaction is catalyzed by a pyruvate kinase. In scheme (3b), the reaction is catalyzed by a lactate dehydrogenase. The $NAD(P)^+$ generated in scheme (3b) can be spectraphotometrically detected at 340 nm.

Any adenosine deaminase can be used for scheme (2). For example, the adenosine deaminase from bovine spleen (Sigma-Aldrich catalog Nos. A5168, 6648 and 5043), from calf intestinal mucosa (Sigma-Aldrich catalog Nos. 01898, A9876 and A1030) or human adenosine deaminase from human erythrocytes (Sigma-Aldrich catalog No. BCR647) can be used. In another example, the adenosine deaminase encoded by the nucleic acids having the GenBank accession No. U76422 (Human, see also Lai, et al., *Mol. Cell. Biol.*, 17(5):2413-24 (1997)) can be used.

Any purine nucleoside phosphorylase can be used for scheme (2b). For example, the purine nucleoside phosphorylase encoded by the nucleic acids having the following GenBank accession Nos. can be used: U88529 (*E. coli*); U24438 (*E. coli*, see also Cornell and Riscoe, *Biochim. Biophys. Acta*, 1396(1):8-14 (1998)); U83703 (*H. pylori*); and M30469 (*E. coli*).

Any xanthine oxidase can be used for scheme (2b). For example, the xanthine oxidase encoded by the nucleic acids having the following GenBank accession Nos. can be used: AF080548 (*Sinorhizobium meliloti*); and U39487 (Human, see also Saksela and Raivio, *Biochem. J.*, 315(1):235-9 (1996)).

Any adenosine kinase can be used for scheme (3). For example, the adenosine kinase encoded by the nucleic acids having the following GenBank accession Nos. can be used: NM_006721 (*Homo sapiens*); NM_001532 (*Homo sapiens*); NM_001123 (*Homo sapiens*); NM_021129 (*Homo sapiens*); and BC003568 (*Homo sapiens*). The adenosine kinase disclosed in U.S. Pat. No. 5,861,294, McNally et al., *Biochem. Biophys. Res. Commun.* 231:645-650 (1997), and Singh et al., *Eur. J. Biochem.* 241:564-571 (1996) can also be used.

Any glutamate dehydrogenase can be used for scheme (2a). For example, the glutamate dehydrogenase (or glutamic acid dehydrogenase) disclosed in Perez-de la Mora et al., *Anal. Biochem.*, 180(2):248-52 (1989) and Gore, *Int. J. Biochem.*, 13(8):879-86 (1981) an be used.

Any pyruvate kinase can be used for scheme (3a). For example, the pyruvate kinase from porcine (Sigma-Aldrich catalog No. K4388), *Bacillus stearothermophilus* (Sigma-Aldrich catalog No. P1903), chicken muscle (Sigma-Aldrich catalog No. P5788) and rabbit muscle (Sigma-Aldrich catalog No. 83330) can be used.

Any lactate dehydrogenase can be used for scheme (3b). For example, the lactate dehydrogenase from Human (Sigma-Aldrich catalog No. BCR404), *Lactobacillus leichmanii* (Sigma-Aldrich catalog No. 61306), *Lactobacillus sp* (Sigma-Aldrich catalog No. 59023) and rabbit muscle (Sigma-Aldrich catalog No. 61311) can be used.

The methods described herein can be used to assay any sample, e.g., a body fluid or a biological tissue. Exemplary body fluids include urine, blood, plasma, serum, saliva, semen, stool, sputum, cerebral spinal fluid, tears, mucus and amniotic fluid. Preferably, the body fluid to be assayed is blood. The blood sample can be assayed directly or be treated before assaying. For example, the blood sample can be further separated into a plasma or serum fraction.

Prior to or concurrently with the contact between the sample and the Hcy co-substrate and the Hcy converting enzyme, oxidized or conjugated Hcy in the sample can be converted into reduced Hcy. In the plasma or urine, significant proportions of the homocysteine present may be bound by disulphide linkage to circulating proteins, such as albumin, and homocysteine may also be present in the form of other disulphide derivatives (generally homocysteine—cysteine conjugates). To obtain an estimate of total homocysteine present in the sample it may therefore be desirable to treat the sample with a reducing agent to cleave the disulphide bonds and liberate free homocysteine.

Any suitable reducing agent can be used. Disulphides are easily and specifically reduced by thiols (e.g. tri-n-butylphosphine (TBP), dithiothreitol (DTT), dithioerythritol (DTE), 2-mercapto-ethanol, cysteine-thioglycolate, thioglycolic acid, tris(2-carboxyethyl)phosphine, free metals, glutathione and similar compounds). Direct chemical reduction can be achieved using borohydrides (e.g. sodium borohydride) or amalgams (e.g. sodium amalgam) or more specialized reagents such as phosphines or phosphorothioates can be used. Disulphide reduction is reviewed by Jocelyn in Methods of Enzymology 143: 243-256 (1987) where a wide range of suitable reducing agents is listed. The reducing agent can also be tris(2-carboxyethyl)-phosphine hydrochloride (TCEP). Preferably, the dithiothreitol or TCEP is provided in a concentration of up to approximately 30 mM.

The method of the invention may further comprise a step of removing the reducing agent used to convert oxidized or conjugated Hcy into reduced Hcy prior to or concurrently with contacting the sample with the Hcy co-substrate and the Hcy converting enzyme. For example, the reducing agent can be removed by addition of N-ethylmaleimide or other thio-reacting compounds C. Kits for Assaying Homocysteine In another aspect, the present invention is directed a kit for assaying Hcy in a sample, which kit comprises: a) a Hcy converting enzyme; b) a Hcy co-substrate; and c) a reagent for assessing Hcy co-substrate conversion product. In each embodiment, the kit can be packaged and can further comprise instructions for using the items in the kit to practice a method of the invention.

In some embodiments, the Hcy co-substrate is S-adenosylmethionine (SAM), the Hcy converting enzyme is a S-adenosylmethionine (SAM)-dependent homocysteine S-methyltransferase, and the Hcy co-substrate conversion product is S-adenosyl-L-homocysteine (SAH). In some embodiments, the reagent for assessing Hcy co-substrate conversion product SAH is an antibody that specifically binds to SAH.

In another aspect, the invention is directed to a kit for assaying Hcy in a sample, which kit comprises: a) a S-adenosylmethionine (SAM)-dependent homocysteine S-methyltransferase; b) S-adenosylmethionine (SAM), or ATP, methionine and a SAM synthase; c) a SAH hydrolase; and d) a reagent for assessing adenosine (Ado).

In another aspect, the invention is directed to a kit for assaying Hcy in a sample, which kit comprises: a) a S-adenosylmethionine (SAM)-dependent homocysteine S-methyltransferase; b) S-adenosylmethionine (SAM), or ATP, methionine, and a SAM synthase; c) a SAH nucleosidase; and d) a reagent for assessing adenine. The kit can further comprise S-ribosyl homocysteinase.

A reagent for assessing adenine can be adenine deaminase or adenine phosophoribosyltransferase or 5-phospho-a-D-ribose 1-diphosphate, or xanthine oxidase, or glutamate dehydrogenase, or a reagent for detecting ammonia formed from adenine, which reagent can be alpha-ketoglutarate and/or glutamate dehydrogenase and/or NADH.

In still another aspect, the invention is directed to a kit for assaying Hcy in a sample, which kit comprises: a) a S-adenosylmethionine (SAM)-dependent homocysteine S-methyltransferase; b) S-adenosylmethionine (SAM); and c) a reagent for assessing SAH, wherein the kit does not comprise an enzyme or a reagent for generating $H_2O_2$ and a reagent for detecting $H_2O_2$.

In some embodiments, the reagent for assessing Ado comprises an adenosine converting enzyme other than the SAH hydrolase. In some embodiments, the adenosine converting enzyme is an adenosine kinase. In other embodiments, the adenosine converting enzyme is an adenosine deaminase.

The kit described herein can further comprise a reducing agent, e.g., dithiothreitol or tris(2-carboxyethyl)-phosphine hydrochloride (TCEP).

The kits of the invention may be in any suitable packaging. For example, the packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays described herein.

D. Examples

The following examples are included for illustrative purposes only and are not intended to limit the scope of the invention.

Example 1

GLDH-NADH Coupling to Detect $NH_4^+$ Generated by the Enzymatic Cycling Using Purified SAM In this study, the following coupled enzymatic cycling reactions are used:

In scheme (1), the reaction is catalyzed by a SAM-dependent homocysteine S-methyltransferase. In scheme (2), the reaction is catalyzed by a SAH hydrolase. In scheme (3), the reaction is catalyzed by an adenosine deaminase. In scheme (4), the reaction is catalyzed by a L-glutamate dehydrogenase. The $NAD(P)^+$ is spectraphotometrically detected at 340 nm. A more detailed description of the reagents used in this study is set forth in the following Tables 1 and 2.

TABLE 1

Compositions of Reagent 1

| Chemical Reagent 1 | Concentration |
|---|---|
| Potassium phosphate | 15 mM |
| NAD(P)H | 5 mM |
| GLDH | 2 KU/L |
| BSA | 1.2 g/L |
| Adenosine Deaminase | 50 KU/L |
| Homocysteine methyltransferase | 10 KU/L |
| DTT | 0.2 mM |
| α-ketoglutarate | 30 mM |
| SAM | 3 mM |

TABLE 2

Compositions of Reagent 2

| Chemicals Reagent 2 | Concentration |
|---|---|
| Tris-HCl | 15 mM |
| BSA | 1.2 g/L |
| SAH hydrolase | 10 KU/L |

Figure 2:
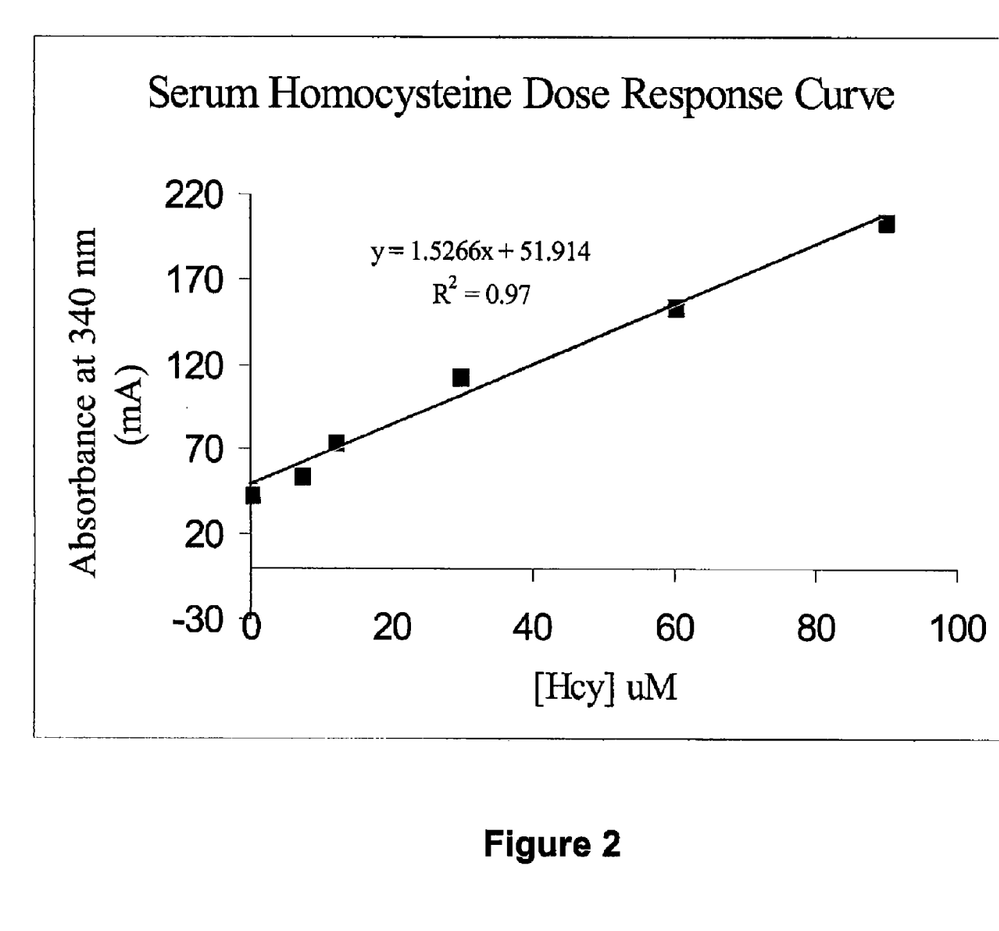
FIG. 2 depicts a serum homocysteine dose response curve obtained in the experiment described in Example 1.

In this study, 180 µl of reagent 1 was mixed with 20 µl of a serum or plasma sample to be tested and the mixture was incubated at 37° C. for 5 minutes. Sixty (60) µl of reagent 2 was then added to the mixture and was incubated at 37° C. for another 5 minutes. The change of the absorbance at 340 nm was measured for 2-5 minutes after the reagent 2 was added. One exemplary test result was shown in FIG. 2.

Example 2

GLDH-NADH Coupling to Detect $NH_4^+$ Generated by the Enzymatic Cycling Using SAM Concurrently Converted by SAM Synthase from ATP and Methionine In this study, the following coupled enzymatic cycling reactions are used:

In scheme (1), the reaction is catalyzed by a SAM Synthase. In scheme (2), the reaction is catalyzed by a SAM-dependent homocysteine S-methyltransferase. In scheme (3), the reaction is catalyzed by a SAH hydrolase. In scheme (4), the reaction is catalyzed by an adenosine deaminase. In scheme (5), the reaction is catalyzed by a L-glutamate dehydrogenase. The NAD(P)$^+$ is spectraphotometrically detected at 340 nm. A more detailed description of the reagents used in this study is set forth in the following Tables 3 and 4.

TABLE 3

Compositions of Reagent 3

| Chemical Reagent 3 | Concentration |
| --- | --- |
| Good's buffer | 15 mM |
| NAD(P)H | 5 mM |
| GLDH | 2 KU/L |
| BSA | 1.2 g/L |
| TCEP | 0.2 mM |
| α-ketoglutarate | 30 mM |
| ATP | 10 mM |
| Methionine | 5 mM |
| SAM Synthase | 10 KU/L |
| Adenosine deaminase | 50 KU/L |
| Homocysteine methyltransferase | 20 KU/L |
| ZnCl$_2$ | 10 mM |

TABLE 4

Compositions of Reagent 4

| Chemicals Reagent 4 | Concentration |
| --- | --- |
| Sodium phosphate | 15 mM |
| BSA | 1.2 g/L |
| SAH hydrolase | 10 KU/L |

In this study, 270 μl of reagent is mixed with 20 μl of a serum or plasma sample to be tested and the mixture is incubated at 37° C. for 5 minutes. Sixty (90) μl of reagent 2 is then added to the mixture and was incubated at 37° C. for another 5 minutes. The change of absorbance at 340 nm is measured for 2-5 minutes after the reagent 2 is added.

Example 3

Adenosine Kinase—Pyruvate Kinase—Lactate Dehydrogenase—NADH Coupling to Detect Adenosine Generated by the Enzymatic Cycling In this study, the following coupled enzymatic cycling reactions are used:

SAM + Hcy ⟶ SAH + Methionine (1)

(2)

Adenosine + ATP ⟶ ADP + AMP (3)

ADP + PEP ⟶ Pyruvate + ATP (4)

Pyruvate + NADH ⟶ Lactate + NAD (5)

In scheme (1), the reaction is catalyzed by a SAM-dependent homocysteine S-methyltransferase. In scheme (2), the reaction is catalyzed by a SAH hydrolase. In scheme (3), the reaction is catalyzed by an adenosine kinase. In scheme (4), the reaction is catalyzed by a pyruvate kinase. In scheme (5), the reaction is catalyzed by a lactate dehydrogenase. The NAD(P)$^+$ is spectraphotometrically detected at 340 nm. A more detailed description of the reagents used in this study is set forth in the following Tables 5 and 6.

TABLE 5

Compositions of Reagent 5

| Chemical Reagent 5 | Concentration |
| --- | --- |
| Potassium phosphate | 15 mM |
| NADH | 5 mM |
| GLDH | 2 KU/L |
| BSA | 1.2 g/L |
| Adenosine Kinase | 10 KU/L |
| Homocysteine methyltransferase | 10 KU/L |
| DTT | 0.2 mM |
| MgCl$_2$ | 15 mM |
| Pyruvate Kinase | 5 KU/L |
| Lactate Dehydrogenase | 25 KU/L |
| SAM | 3 mM |

TABLE 6

Compositions of Reagent 6

| Chemicals Reagent 6 | Concentration |
| --- | --- |
| Tris-HCl | 15 mM |
| BSA | 1.2 g/L |
| SAH hydrolase | 10 KU/L |

In this study, 180 μl of reagent is mixed with 20 μl of a serum or plasma sample to be tested and the mixture is incubated at 37° C. for 5 minutes. Sixty (60) μl of reagent 2 is then added to the mixture and was incubated at 37° C. for another 5 minutes. The change of absorbance at 340 nm is measured for 2-5 minutes after the reagent 2 is added.

Example 4

Using SAH Nucleosidase to Convert SAH into Adenine and S-Ribosyl Homocysteine, and Cycling S-Ribosyl Homocysteine with S-Ribosyl Homocysteinase In this method, the following cycling system is used:

This method converts SAM and Hcy into SAH and L-methionine, and uses SAH nucleosidase and S-ribosyl homocysteinase to cycle the SAH back into Hcy to complete the cycle. It forms L-methionine as a homocysteine conversion product. The co-substrate conversion product SAH is then detected by its conversion into S-ribosyl homocysteine and adenine: S-ribosyl homocysteine is used in the cycling assay, and the Adenine formed can be detected in a variety of ways. The following Scheme illustrates certain of the options for assessing adenine.

Adenine is detected by conversion into AMP and diphosphate, whereupon AMP or diphosphate is assessed by methods known in the art such as use of selective antibodies for AMP. Alternatively, adenine is converted by adenine deaminase into hypoxanthine and ammonia, whereupon hypoxanthine is detected by assessing hydrogen peroxide formed when hypoxanthine is converted by xanthine oxidase into xanthine. Alternatively, ammonia is detected by monitoring the consumption of NADH, when ammonia reacts with an acceptor such as alpha-ketoglutarate in the presence of an amination enzyme such as glutamate dehydrogenase. The latter methods permit a user to assess the adenine formed in this cycling assay by spectrophotometric methods that are well established in the art and are conveniently automated.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The claimed invention is:

1. A method for assaying homocysteine (Hcy) in a sample without chromatographic separation, which method comprises:
   a) contacting a sample containing or suspected of containing Hcy with a Hcy co-substrate and a Hcy converting enzyme in a Hcy conversion reaction to form a Hcy conversion product and a Hcy co-substrate conversion product, wherein the Hcy co-substrate is S-adenosylmethionine (SAM), the Hcy converting enzyme is a S-adenosylmethionine (SAM)-dependent homocysteine S-methyltransferase, the Hcy conversion product is methionine (Met) and the Hcy co-substrate conversion product is S-adenosyl-L-homocysteine (SAH);
   b) contacting the mixture formed in step a) with an adenosylhomocysteine nucleosidase to convert SAH into adenine and S-ribosyl homocysteine;
   c) contacting the mixture formed in step b) with an S-ribosyl homocysteinase to cycle the S-ribosyl homocysteine into homocysteine; and
   d) assessing the amount of adenine in the mixture formed in step b) and/or c),
   whereby the amount of Hcy in the sample is determined from the amount of adenine.

2. The method of claim 1, wherein the step of assessing the amount of adenine comprises the step of converting the adenine by adenine deaminase into ammonia and hypoxanthine, wherein the amount of at least one of ammonia and hypoxanthine is assessed in order to assess the amount of adenine.

3. The method of claim 2, wherein the assessment of the amount of adenine comprises assessing the amount of ammonia formed.

4. The method of claim 3, wherein the amount of ammonia formed is measured by assessing appearance of NAD+ or disappearance of NADH when ammonia is converted into glutamate by the action of glutamate dehydrogenase.

5. The method of claim 2, wherein the amount of adenine is assessed by assessing the amount of hypoxanthine formed.

6. The method of claim 5, wherein the amount of hypoxanthine is assessed by monitoring its conversion into xanthine, which conversion is catalyzed by xanthine oxidase.

7. The method of claim 1, wherein the amount of adenine is assessed by monitoring the formation of either or both of AMP and diphosphate catalyzed by the action of adenine phosphoribosyltransferase acting on the adenine and 5-phospho-α-D-ribose 1-diphosphate (PRPP).

8. The method of claim 1, wherein the sample is a body fluid or a biological tissue.

9. The method of claim 8, wherein the body fluid is selected from the group consisting of urine, blood, plasma, serum, saliva, semen, stool, sputum, cerebral spinal fluid, tears, mucus and amniotic fluid.

10. The method of claim 8, wherein the body fluid is blood.

11. The method of claim 10, wherein the blood sample is further separated into a plasma or serum fraction.

12. The method of claim 1, wherein the SAM is produced from ATP and methionine by a SAM synthase.

13. The method of claim 1, wherein prior to or concurrently with the contact between the sample and the Hcy co-substrate and the Hcy converting enzyme, oxidized or conjugated Hcy in the sample is converted into reduced Hcy.

14. The method of claim 1, wherein the amount of adenine is assessed without chromatographic separation.

15. A method for assaying homocysteine (Hcy) in a sample, which method comprises:
   a) contacting a sample containing or suspected of containing Hcy with a Hcy co-substrate and a Hcy converting enzyme in a Hcy conversion reaction to form a Hcy conversion product and a Hcy co-substrate conversion product, wherein the Hcy co-substrate is S-adenosylmethionine (SAM), the Hcy converting enzyme is a S-adenosylmethionine (SAM)-dependent homocysteine S-methyltransferase, the Hcy conversion product is methionine (Met) and the Hcy co-substrate conversion product is S-adenosyl-L-homocysteine (SAH),
   b) contacting the SAH generated in step (a) with SAH nucleosidase and S-ribosyl homocysteinase to generate Hcy, which is cycled into the Hcy conversion reaction by the SAM-dependent homocysteine S-methyltransferase to form a Hcy co-substrate based enzyme cycling reaction system, and adenine; and
   c) assessing the adenine formed to assess the presence or amount of Hcy in the sample.

16. The method of claim 15, wherein the assessment of adenine does not involve an enzymatic reaction generating $H_2O_2$ and detection of $H_2O_2$.

17. A kit for assaying Hcy in a sample, which kit comprises:
 a) a S-adenosylmethionine (SAM)-dependent homocysteine S-methyltransferase;
 b) S-adenosylmethionine (SAM);
 c) a SAH nucleosidase;
 d) a reagent for assessing adenine; and
 e) S-ribosyl homocysteinase.

18. The kit of claim 17, wherein the reagent for assessing adenine comprises an adenine converting enzyme other than SAH hydrolase.

19. The kit of claim 18, wherein the adenine converting enzyme is an adenine deaminase.

20. The kit of claim 18, wherein the adenine converting enzyme is an adenine phosphoribosyltransferase.

* * * * *